United States Patent
Zhou et al.

(10) Patent No.: US 10,517,864 B2
(45) Date of Patent: *Dec. 31, 2019

(54) SUSTAINED-RELEASE BUPRENORPHINE SOLUTIONS

(71) Applicant: Indivior UK Limited, Slough Berkshire (GB)

(72) Inventors: Mingxing Zhou, Fort Collins, CO (US); Richard L. Norton, Fort Collins, CO (US)

(73) Assignee: INDIVIOR UK LIMITED, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/016,186

(22) Filed: Jun. 22, 2018

(65) Prior Publication Data

US 2019/0022085 A1 Jan. 24, 2019

Related U.S. Application Data

(63) Continuation of application No. 15/125,052, filed as application No. PCT/GB2015/050676 on Mar. 9, 2015, now Pat. No. 10,022,367.

(30) Foreign Application Priority Data

Mar. 10, 2014 (GB) .................. 1404139.6

(51) Int. Cl.
| | |
|---|---|
| *A61K 31/485* | (2006.01) |
| *A61K 9/08* | (2006.01) |
| *A61K 9/00* | (2006.01) |
| *A61K 47/10* | (2017.01) |
| *A61K 47/22* | (2006.01) |

(52) U.S. Cl.
CPC .......... *A61K 31/485* (2013.01); *A61K 9/0019* (2013.01); *A61K 9/08* (2013.01); *A61K 47/10* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 3,466,362 A | 9/1969 | Klaui et al. | |
| 4,534,974 A | 8/1985 | Kim | |
| 4,573,995 A | 3/1986 | Chen et al. | |
| 4,599,354 A | 7/1986 | Shulman | |
| 4,626,539 A | 12/1986 | Aungst et al. | |
| 4,755,389 A | 7/1988 | Jones et al. | |
| 4,784,855 A | 11/1988 | Yamashita et al. | |
| 4,804,663 A | 2/1989 | Kennis et al. | |
| 4,938,763 A | 7/1990 | Dunn et al. | |
| 5,008,110 A | 4/1991 | Benecke et al. | |
| 5,026,556 A | 6/1991 | Drust et al. | |
| 5,069,909 A | 12/1991 | Sharma et al. | |
| 5,096,715 A | 3/1992 | Sinclair | |
| 5,173,304 A | 12/1992 | Lohner et al. | |
| 5,324,519 A | 6/1994 | Dunn et al. | |
| 5,346,903 A | 9/1994 | Ackerman et al. | |
| 5,453,425 A | 9/1995 | Francois et al. | |
| 5,486,362 A | 1/1996 | Kitchell et al. | |
| 5,616,587 A | 4/1997 | Francois et al. | |
| 5,648,093 A | 7/1997 | Gole et al. | |
| 5,688,801 A | 11/1997 | Mesens et al. | |
| 5,702,716 A | 12/1997 | Dunn et al. | |
| 5,744,153 A | 4/1998 | Yewey et al. | |
| 5,770,231 A | 6/1998 | Mesens et al. | |
| 5,780,044 A | 7/1998 | Yewey et al. | |
| 5,792,477 A | 8/1998 | Rickey | |
| 5,948,787 A | 9/1999 | Merrill et al. | |
| 5,990,194 A | 11/1999 | Dunn et al. | |
| 6,004,969 A | 12/1999 | Hu | |
| 6,120,789 A | 9/2000 | Dunn | |
| 6,224,905 B1 | 5/2001 | Lawrence et al. | |
| 6,261,583 B1 | 7/2001 | Dunn et al. | |
| 6,264,987 B1 | 7/2001 | Wright et al. | |
| 6,284,274 B1 | 9/2001 | Merrill et al. | |
| 6,294,192 B1 | 9/2001 | Patel et al. | |
| 6,303,137 B1 | 10/2001 | Dittgen et al. | |
| 6,355,657 B1 | 3/2002 | Osborne | |
| 6,383,471 B1 | 5/2002 | Chen et al. | |
| 6,395,293 B2 | 5/2002 | Polson et al. | |
| 6,413,536 B1 | 7/2002 | Gibson et al. | |
| 6,528,080 B2 | 3/2003 | Dunn et al. | |
| 6,565,874 B1 | 5/2003 | Dunn et al. | |

(Continued)

FOREIGN PATENT DOCUMENTS

| | | |
|---|---|---|
| CN | 101014319 A | 8/2007 |
| CN | 101014319 B | 8/2007 |

(Continued)

OTHER PUBLICATIONS

Ahmed, T.A. et al. (Oct. 2012, e-published Jun. 29, 2012). "Development of biodegradable in situ implant and microparticle injectable formulations for sustained delivery of haloperidol," *J Pharm Sci* 101(10):3753-3762.

Ahmed, T.A. et al. (Jun. 2015, e-published Mar. 20, 2014). "Biodegradable injectable in situ implants and microparticles for sustained release of montelukast: in vitro release, pharmacokinetics, and stability," *AAPS PharmSciTech* 15(3):772-780.

Babu, R.J. et al. (May-Jun. 2005). "Effect of penetration enhancers on the transdermal delivery of bupranolol through rat skin," *Drug Deliv* 12(3):165-169.

Buggins, T.R. et al. (Dec. 22, 2007). "The effects of pharmaceutical excipients on drug disposition," *Adv Drug Deliv Rev* 59(15):1482-1503.

(Continued)

*Primary Examiner* — Samantha L Shterengarts
(74) *Attorney, Agent, or Firm* — Edward D. Grieff; Mintz, Levin, Cohn, Ferris, Glovsky and Popeo, P.C.

(57) ABSTRACT

The disclosure provides extended release pharmaceutical formulations comprising an opioid, particularly buprenorphine, a biocompatible organic solvent, and, optionally, a glycol, for use in the treatment of pain or opioid dependence. The pharmaceutical formulations are in the form of a pharmaceutical solution.

22 Claims, 4 Drawing Sheets

(56) References Cited

U.S. PATENT DOCUMENTS

| | | |
|---|---|---|
| 6,596,316 B2 | 7/2003 | Lyons et al. |
| 6,630,155 B1 | 10/2003 | Chandrashekar et al. |
| 7,041,320 B1 | 5/2006 | Nuwayser |
| 7,410,635 B2 | 8/2008 | Blondino et al. |
| 7,501,113 B2 | 3/2009 | Blondino et al. |
| 7,691,408 B2 | 4/2010 | Leroux et al. |
| 8,114,383 B2 | 2/2012 | Bartholomaus et al. |
| 8,114,429 B2 | 2/2012 | Michal et al. |
| 8,133,507 B2 | 3/2012 | Yum et al. |
| 8,173,148 B2 | 5/2012 | Dadey et al. |
| 8,221,778 B2 | 7/2012 | Siegel et al. |
| 8,236,755 B2 | 8/2012 | Thuresson et al. |
| 8,257,722 B2 | 9/2012 | Michal et al. |
| 8,313,763 B2 | 11/2012 | Margaron et al. |
| 8,324,343 B2 | 12/2012 | Moore et al. |
| 8,329,203 B2 | 12/2012 | Siegel et al. |
| 8,333,989 B2 | 12/2012 | Sukuru |
| 8,377,479 B2 | 2/2013 | Talton |
| 8,415,401 B2 | 4/2013 | Yum et al. |
| 8,512,749 B2 | 8/2013 | Sawhney et al. |
| 8,563,023 B2 | 10/2013 | Michal et al. |
| 8,574,552 B2 | 11/2013 | Stroppolo et al. |
| 8,586,103 B2 | 11/2013 | Li et al. |
| 8,815,944 B2 | 8/2014 | Leroux et al. |
| 8,852,638 B2 | 10/2014 | Luk et al. |
| 8,877,241 B2 | 11/2014 | Fischer et al. |
| 8,916,202 B2 | 12/2014 | Lebon et al. |
| 8,921,387 B2 | 12/2014 | Norton et al. |
| 8,975,270 B2 | 3/2015 | Norton et al. |
| 9,017,709 B2 | 4/2015 | Griguol et al. |
| 9,044,450 B2 | 6/2015 | Luk et al. |
| 9,168,216 B2 | 10/2015 | Gavin et al. |
| 9,221,831 B2 | 12/2015 | Kyle et al. |
| 9,254,268 B2 | 2/2016 | Krayz et al. |
| 9,259,872 B2 | 2/2016 | Hayes et al. |
| 9,272,044 B2 | 3/2016 | Norton et al. |
| 9,295,645 B2 | 3/2016 | Norton et al. |
| 9,308,162 B2 | 4/2016 | Norton |
| 9,326,979 B2 | 5/2016 | Kimura et al. |
| 9,364,518 B2 | 6/2016 | Nadkarni et al. |
| 9,415,034 B2 | 8/2016 | Oliver et al. |
| 9,468,599 B2 | 10/2016 | Ray, II et al. |
| 9,498,432 B2 | 11/2016 | Norton et al. |
| 9,555,226 B2 | 1/2017 | Zumbrunn et al. |
| 9,597,402 B2 | 3/2017 | Luk et al. |
| 9,782,402 B2 | 10/2017 | Norton et al. |
| 9,827,241 B2 | 11/2017 | Norton et al. |
| 10,022,367 B2 | 7/2018 | Zhou et al. |
| 2003/0004100 A1 | 1/2003 | Dasch et al. |
| 2003/0068375 A1 | 4/2003 | Wright et al. |
| 2003/0129219 A1 | 7/2003 | Hong et al. |
| 2003/0211157 A1 | 11/2003 | Simon |
| 2004/0018238 A1 | 1/2004 | Shukla |
| 2004/0033250 A1 | 2/2004 | Patel et al. |
| 2004/0101557 A1 | 5/2004 | Gibson et al. |
| 2004/0138237 A1 | 7/2004 | Shah |
| 2004/0151670 A1 | 8/2004 | Blondino et al. |
| 2005/0032781 A1 | 2/2005 | Ehrich |
| 2005/0048115 A1 | 3/2005 | Mangena et al. |
| 2005/0048123 A1 | 3/2005 | Su et al. |
| 2005/0053647 A1 | 3/2005 | Matusch et al. |
| 2005/0112067 A1 | 5/2005 | Kumar et al. |
| 2006/0002979 A1 | 1/2006 | Ashammakhi et al. |
| 2006/0003008 A1 | 1/2006 | Gibson et al. |
| 2006/0210604 A1 | 9/2006 | Dadey et al. |
| 2007/0077304 A1 | 4/2007 | Luk et al. |
| 2007/0117828 A1 | 5/2007 | Simmons et al. |
| 2007/0265190 A1 | 11/2007 | Thuresson et al. |
| 2008/0020011 A1 | 1/2008 | Finkelstein et al. |
| 2008/0020039 A1 | 1/2008 | Parikh et al. |
| 2008/0299168 A1 | 12/2008 | Dadey et al. |
| 2009/0048145 A1 | 2/2009 | Hellerbrand et al. |
| 2009/0061011 A1 | 3/2009 | Talton |
| 2009/0074708 A1 | 3/2009 | Oliver et al. |
| 2009/0092650 A1 | 4/2009 | Warren et al. |
| 2009/0202481 A1 | 8/2009 | Li et al. |
| 2009/0246265 A1 | 10/2009 | Stinchcomb et al. |
| 2010/0098735 A1 | 4/2010 | Jain et al. |
| 2010/0173940 A1 | 7/2010 | Leichs et al. |
| 2010/0266655 A1 | 10/2010 | Dadey |
| 2010/0292195 A1 | 11/2010 | Dadey et al. |
| 2010/0330150 A1 | 12/2010 | Venkatesh et al. |
| 2011/0229526 A1 | 9/2011 | Rosenberg et al. |
| 2011/0230816 A1 | 9/2011 | Copp-Howland |
| 2012/0058158 A1 | 3/2012 | Booles |
| 2012/0207843 A1 | 8/2012 | Lebon et al. |
| 2013/0023553 A1 | 1/2013 | Jude-Fishburn et al. |
| 2013/0129828 A1 | 5/2013 | Talton |
| 2013/0143909 A1 | 6/2013 | Chong et al. |
| 2013/0177603 A1 | 7/2013 | Gutierro Aduriz et al. |
| 2013/0210751 A1 | 8/2013 | Dong et al. |
| 2013/0231359 A1 | 9/2013 | Chong et al. |
| 2013/0331803 A1 | 12/2013 | Fleschhut et al. |
| 2014/0023692 A1 | 1/2014 | Du Toit et al. |
| 2014/0134261 A1 | 5/2014 | Singh et al. |
| 2014/0271869 A1 | 9/2014 | Richey et al. |
| 2014/0363487 A1 | 12/2014 | Hille et al. |
| 2015/0209555 A1 | 7/2015 | Ruane et al. |
| 2015/0231258 A1 | 8/2015 | Luk et al. |
| 2015/0359891 A1 | 12/2015 | Chen et al. |
| 2016/0184296 A1 | 6/2016 | Norton et al. |
| 2016/0303038 A1 | 10/2016 | Yadav et al. |
| 2018/0121137 A1 | 5/2018 | Norton et al. |
| 2018/0157440 A1 | 6/2018 | Norton et al. |

FOREIGN PATENT DOCUMENTS

| | | |
|---|---|---|
| EP | 0 368 409 A2 | 5/1990 |
| EP | 0 368 409 A3 | 5/1990 |
| EP | 0 532 546 A1 | 3/1993 |
| EP | 0 532 546 B1 | 3/1993 |
| EP | 0 572 494 A1 | 12/1993 |
| EP | 0 572 494 B1 | 12/1993 |
| EP | 1 006 935 A1 | 6/2000 |
| EP | 1 006 935 B1 | 6/2000 |
| EP | 1 015 032 A2 | 7/2000 |
| EP | 1 644 002 A1 | 4/2006 |
| EP | 1 644 002 B1 | 4/2006 |
| EP | 1 830 900 A1 | 9/2007 |
| EP | 1 940 351 A2 | 7/2008 |
| EP | 1 940 351 B1 | 7/2008 |
| EP | 2 081 574 A1 | 7/2009 |
| EP | 2 361 609 A1 | 8/2011 |
| EP | 2 361 609 B1 | 8/2011 |
| EP | 2 445 487 A2 | 5/2012 |
| EP | 2 797 602 A2 | 11/2014 |
| GB | 784659 | 10/1957 |
| GB | 806876 | 1/1959 |
| GB | 873526 A | 7/1961 |
| GB | 887872 A | 1/1962 |
| IN | 1535/DEL/2004 | 8/2006 |
| WO | WO-91/19474 | 12/1991 |
| WO | WO-93/23019 A1 | 11/1993 |
| WO | WO-95/27481 A1 | 10/1995 |
| WO | WO-96/21427 A1 | 7/1996 |
| WO | WO-96/39095 A1 | 12/1996 |
| WO | WO-98/58685 A1 | 12/1998 |
| WO | WO-00/06117 A1 | 2/2000 |
| WO | WO-00/024374 A1 | 5/2000 |
| WO | WO-01/15699 | 3/2001 |
| WO | WO-01/35929 A2 | 5/2001 |
| WO | WO-01/35929 A3 | 5/2001 |
| WO | WO-02/30393 A2 | 4/2002 |
| WO | WO-02/30393 A3 | 4/2002 |
| WO | WO-02/038185 A2 | 5/2002 |
| WO | WO-02/038185 A3 | 5/2002 |
| WO | WO-2004/037259 A1 | 5/2002 |
| WO | WO-2003/041684 A2 | 5/2003 |
| WO | WO-2003/041684 A3 | 5/2003 |
| WO | WO-2004/043432 A3 | 5/2004 |
| WO | WO-2006/041942 A2 | 4/2006 |
| WO | WO-2006/041942 A3 | 4/2006 |
| WO | WO-2006/053175 A2 | 5/2006 |
| WO | WO-2006/053175 A3 | 5/2006 |

(56) References Cited

FOREIGN PATENT DOCUMENTS

| | | |
|---|---|---|
| WO | WO-2007/041410 A2 | 4/2007 |
| WO | WO-2007/041410 A3 | 4/2007 |
| WO | WO-2004/043432 A3 | 5/2007 |
| WO | WO-2007/061828 | 5/2007 |
| WO | WO-2007/103185 | 9/2007 |
| WO | WO-2008/045516 A1 | 4/2008 |
| WO | WO-2008/100532 A1 | 8/2008 |
| WO | WO-2008/153611 A2 | 12/2008 |
| WO | WO-2008/153611 A3 | 12/2008 |
| WO | WO-2009/091737 A2 | 7/2009 |
| WO | WO-2009/091737 A3 | 7/2009 |
| WO | WO-2009/127878 A1 | 10/2009 |
| WO | WO-2011/154724 A2 | 12/2011 |
| WO | WO-2011/154724 A3 | 12/2011 |
| WO | WO-2011/154724 A9 | 12/2011 |
| WO | WO-2011/154725 A2 | 12/2011 |
| WO | WO-2011/154725 A3 | 12/2011 |
| WO | WO-2014/016428 A1 | 1/2014 |
| WO | WO-2014/081343 A2 | 5/2014 |
| WO | WO-2014/081343 A3 | 5/2014 |
| WO | WO-2015/136253 A1 | 9/2015 |

OTHER PUBLICATIONS

Cheng, Y. et al. (Dec. 2013, e-published Oct. 1, 2013). "Thermosensitive hydrogels based on polypeptides for localized and sustained delivery of anticancer drugs," *Biomaterials* 34(38):10338-10347.

Dewan, I. et al. (2011). "Study of Release Kinetics of Dexamethasone from Biodegradable PLA In-Situ Implants," *International Journal of Pharmaceutical Science and Research* 2(11):3039-3045.

Furuishi, T. et al. (Jul. 2007). "Effect of permeation enhancers on the in vitro percutaneous absorption of pentazocine," *Biol Pharm Bull* 30(7):1350-1353.

Gou, M. et al. (Apr. 2010). "Polymeric matrix for drug delivery: honokiol-loaded PCL-PEG-PCL nanoparticles in PEG-PCL-PEG thermosensitive hydrogel," *J Biomed Mater Res A* 93(1):219-226.

Ibrahim, H.M. et al. (Jan. 2014, e-published Jan. 9, 2013). "Development of meloxicam in situ implant formulation by quality by design principle," *Drug Dev Ind Pharm* 40(1):66-73.

Jaiswal, J. et al. (Mar. 1, 1999). "Transdermal delivery of naloxone: ex vivo permeation studies," *Int J Pharm* 179(1):129-134.

Kan, P. et al. (Jul. 21, 2005). "Thermogelling Emulsions for Vascular Embolization and Sustained Release Drugs," *Journal of Biomedical Materials Research* 75B(1):185-192.

Karatas, A. et al. (2006). "Studies of Release of Ketorolac Tromethamin and Indomethacin from Opthalmic Hydrogel Inserts," *Ankara Ecz Fak Derg* 35(4)255-268.

Kelava, T. et al. (2011). "Biological Actions of Drug Solvents," *Periodicum Biologorum* 113(3):311-320.

Lin, X. et al. (2012). "A novel risperidone-loaded SAIB-PLGA mixture matrix depot with a reduced burst release: effects of solvents and PLGA on drug release behaviors in vitro/in vivo," *J Mater Sci Mater Med* 23(2):443-455.

Madhu, M. et al. (Nov.-Dec. 2009). "Biodegradeable Injectable Implant Systems for Sustained DeliveryUsing Poly (Lactide-Co-Glycolide) Copolymers," International Journal of Pharmacy and Pharmaceutical Sciences Vol., Suppl 1, 103-107.

Mendelson, J.E. et al (Apr. 2011, e-published Dec. 8, 2010). "Lack of effect of sublingual salvinorin A, a naturally occurring kappa opioid, in humans: a placebo-controlled trial," *Psychopharmacology* 214(4):933-939.

Mownika, G. et al. (2012). "Formulation and Evaluation of Simvastatin Injectable in situ Implants," *American Journal of Drug Discovery and Development* 2(2):87-100.

Nahata, T. et al. (Mar.-Apr. 2009). "Formulation optimization of long-acting depot injection of aripiprazole by using D-optimal mixture design," *PDA J Pharm Sci Technol* 63(2):113-122.

Olby, N. (Sep. 2010). "The pathogenesis and treatment of acute spinal cord injuries in dogs," *Vet Clin North Am Small Anim Pract* 40(5):791-807.

Omidfar, K. et al. (2002). "Stabilization of Penicillinase-Hapten Conjugate for Enzyme Immunoassay," *Journal of Immunoassay & Immunochemistry* 23(3):385-398.

Plourde, F. et al. (Nov. 28, 2005, e-published Sep. 21, 2005). "First report on the efficacy of I-alanine-based in situ-forming implants for the long-term parenteral delivery of drugs," *J Control Release* 108(2-3):433-441.

Pluta, J. et al. (Dec. 20, 2006). "In vitro studies of the properties of thermosensitive systems prepared on Pluronic F-127 as vehicles for methotrexate for delivery to solid tumours," *Polymers in Medicine* 36(3):37-52.

Rackur, H. et al. (2001). "In-Situ Forming Implants of PLGA/Leuprolide Acetate Solutions in NMP and Their in Vitro/In Vivo Release Characteristics," 28$^{th}$ International Symposium on Controlled Release of Bioactive Materials and Fourth Consumer Products Conference, 2001 Proceedings, Abstract 6137, pp. 884-885.

Rafienia, M. et al. (Jul. 2007). "In Vitro Evaluation of Drug Solubility and Gamma Irradiation on the Release of Betamethasone under Simulated In Vivo Conditions," Journal of Bioactive and Compatible Polymers 22:443-459.

Reilley,K.J. et al. (Nov. 17, 2010). "Prevention of Cocaine-Conditioned Place Preference with Salvinorin a Prepared with Optimal Vehicle Conditions," 40$^{th}$ Annual Meeting Neuroscience 2010, Presentation Abstract, 2 pages.

Toot, J.D. et al. *International Journal of Toxicology* 32(1):66.

Wang, L. et al. (May 10, 2012, e-published Feb. 23, 2012). "Design of a long-term antipsychotic in situ forming implant and its release control method and mechanism," *Int J Pharm* 427(2):284-292.

Wischke, C. et al. (Oct. 2010, e-published Jul. 29, 2010). "Development of Plga-based injectable delivery systems for hydrophobic fenretinide," *Pharm Res* 27(10:2063-2074.

Wu, Z. et al. (Oct. 2014, e-published Jul. 1, 2014). "Thermosensitive hydrogel used in dual drug delivery system with paclitaxel-loaded micelles for in situ treatment of lung cancer," *Colloids Surf B Biointerfaces* 122:90-98.

Yaksh, T.L. et al. (1991). "The utility of 2-hydroxpropyl-beta-cyclodextrin as a vehicle for the intracerebral and intrathecal administration of drugs," *Life Sci* 48(7):623-633.

Yang, Y. et al. (May 2012, e-published Mar. 15, 2012). "Improved initial burst of estradiol organogel as long-term in situ drug delivery implant: formulation, in vitro and in vivo characterization," *Drug Dev Ind Pharm* 38(5):550-556.

Yehia, S.A. et al. (Jun. 2012, e-published Nov. 18, 2011). "A novel injectable in situ forming poly-DL-lactide and DL-lactide/glycolide implant containing lipospheres for controlled drug delivery," *J Liposome Res* 22(2):128-138.

Aird, J. (Apr. 2003). Controlled Release—SMi Conference. Feb. 12-13, 2003, London,UK,*IDrugs* 6(4):334-336.

Baker, D.L. et al. (Oct. 2004). "Gonadotropin-releasing hormone agonist: a new approach to reversible contraception in female deer," *J Wildl Dis* 40(4):713-724.

Basu, S.K. et al. (Mar. 2004). "Protein crystals for the delivery of biopharmaceuticals," *Expert Opin Biol Ther* 4(3):301-317.

Berges, R. et al. (2005). "Eligard®: Pharmacokinetics, effect on Testosterone and PSA Levels and Tolerability," *European Urology Supplements* 4:20-25.

Bowersock, T.L. et al. (1999). "Vaccine delivery to animals," *Adv Drug Deliv Rev* 38(2):167-194.

Bromberg, L.E. et al. (Jul. 31, 2000). "Sustained release of silver from periodontal wafers for treatment of periodontitis," *J Control Release* 68(1):63-72.

Chandrashekar, B.L. et al. (Jul. 1999). "Sustained Release of Leuprolide Acetate from an In-situ Forming Biodegradable Polymeric Implant as the Delivery Vehicle," *Proceed Int'l Symp Control Rel Bioact Mater* 26, 3 pages.

Chen, F.A. et al. (Jul. 2003). "Biodegradable polymer-mediated intratumoral delivery of cisplatin for treatment of human head and neck squamous cell carcinoma in a chimeric mouse model," *Head Neck* 25(7):554-560.

Coonts, B.A. et al. (Oct. 1993). "Plasma Concentrations of Naltrexone Base Following Subcutaneous and Intramuscluar Injections of Atrigel™

(56) References Cited

OTHER PUBLICATIONS

Formulations in Dogs," *Pharmaceutical Research: Official Journal of the American Association of Pharmaceutical Scientists* PHREEB 10(10):PDD 7071, 2 pages.

Cox, M.C. et al. (Aug. 2005). "Leuprolide acetate given by a subcutaneous extended-release injection: less of a pain?" *Expert Rev Anticancer Ther* 5(4):605-611.

Dernell, W.S. et al. (1998). "Apparent interaction of dimethyl sulfoxide with cisplatin released from polymer delivery devices injected subcutaneously in dogs," *J Drug Target* 5(5):391-396.

Dunn, R.S., (2003). "The Atrigel Drug Delivery System," *Modified-Release Drug Delivery Technology*, Edited by Rathbone, Hadgraft, Roberts, Marcel Dekker, Inc., Chapter 54, pp. 647-655.

Dunn, R.L. et al (1996). "Sustained Release of Cisplatin in Dogs from an Injectable Implant Delivery System," *Journal of Bioactive and Compatible Polymers*, 11:286-300.

Duysen, E.G. et al (1992). "Bioactivity of Polypeptide Growth Factors Released from the ATRIGEL Drug Delivery System," *PHREEB*, 9(10):S73, Abstract No. 2028.

Duysen, E.G. et al (1993). "Release of Bioactive Growth Factors from the ATRIGEL Delivery System in Tibial Defect and Dermal Wound Models," *PHREEB*, 10(10):S83, Abstract No. 2043.

Duysen, E.G. et al (1994). "An Injectable, Biodegradable Delivery System for Antineoplastic Agents," *PHREEB*, 11(10):S88, Abstract No. 2071.

Erickson, N.M. et al. (2001). "An In Vitro Degradation Study Comparing Poly (DL-Lactide-Co-Glycolide) with Acid End Groups and Ester End Groups," $20^{th}$ Southern Biomedical Engineering Conference, 1 page.

Evans, H.C., et al (2004). "Leuprorelin: Subcutaneous Depot Formulation (ELIGARD) for Advanced Prostate Cancer," *Am J. Cancer*, 3(3):197-201.

Graves, R.A. et al. (Aug. 3, 2007). "In vitro dissolution method for evaluation of buprenorphine in situ gel formulation: a technical," *AAPS PharmSciTech* 8(3): Article 62, E1-E4.

Frank, K.R. et al (1994). "Controlled Release of Bioactive Growth Factors from a Biodegradable Delivery System," PHREEB, 11(10):S88, Abstract No. 2070.

Gerentes, P. et al. (2002). "Study of a chitin-based gel as injectable material in periodontal surgery," *Biomaterials* 23(5):1295-1302.

Griffeth, R.J. et al. (2002). "Is Lucteal Production of $PGF_2\alpha$ Required for Luteolysis?" *Biology of Reproduction* 66(Supplement 1), Abstract 465, 2 pages.

Jain, R.A. (Dec. 2000). "The manufacturing techniques of various drug loaded biodegradable poly(lactide-co-glycolide) (PLGA) devices," *Biomaterials* 21(23):2475-2490.

Jarr, E.M. et al. (Jul. 1999). "Sustained Release of Lidocaine from an Injectable Implant System for Treatmenr of Post-Operative," *Proceedings Int'l Symp Control Rel Bioact Materials* Abstract #5423, 4 pages.

Kaul, S. et al. (Feb. 2000). "Polymeric-based perivascular delivery of a nitric oxide donor inhibits intimal thickening after balloon denudation arterial injury: role of nuclear factor-kappaB," *J Am Coll Cardiol* 35(2):493-501.

Kissel, T. (Jan. 2002). "ABA-triblock copolymers from biodegradable polyester A-blocks and hydrophilic poly(ethylene oxide) B-blocks as a candidate for in situ forming hydrogel delivery systems for proteins," *Adv Drug Deliv Rev* 54(1):99-134.

Kranz, H. et al. (Jan. 5, 2001). "Myotoxicity studies of injectable biodegradable in-situ forming drug delivery systems," *Int J Pharm* 212(1):11-18.

Lynch, G.S. et al. (Nov. 204). "Emerging drugs for sarcopenia: age-related muscle wasting," *Expert Opin Emerg Drugs* 9(2);345-361.

Malik, K. et al. (2010). "Atrigel: A Potential Parenteral Controlled Drug Delivery System," *Der Pharmacia Sinica* 1(1):74-81.

Matschke, C. et al. (Dec. 2007). "Sustained-release injectables formed in situ and their potential use for veterinary products," *J Control Release* 85(1-3):1-15.

McLeod, D.G. et al. (Feb. 2003). "Hormonal therapy: historical perspective to future directions," *Urology* 61(2 Suppl 1):3-7.

Mealy (2004). "Treatment of Metabolic Disorders by Condition," Annual Update 2003/2004—*Drugs of the Future* 29(8):843-872.

Medicott, N.J. et al. (Jun. 23, 2004). "Sustained release veterinary parenteral products," *Adv Drug Deliv Rev* 56(10):1345-1365.

Mottu, F. et al. (Apr. 2000). "In vitro assessment of new embolic liquids prepared from preformed polymers and water-miscible solvents for aneurysm treatment," *Biomaterials* 21(8):803-811.

Packhaeuser, C.B. et al. (Sep. 2004). "In situ forming parenteral drug delivery systems: an overview," *Eur J Pharm Biopharm* 58(2):445-455.

Panaccione, C. et al. (1997). "Use of a Trinomial Distribution Probability Model in Development of a Tier-Testing Scheme for Content Uniformity Testing," *Drug Information Journal* 31:903-909.

Pechenov, S. et al. (Apr. 16, 2004). "Injectable controlled release formulations incorporating protein crystals," *J Control Release* 96(1):149-158.

Perez-Marrero, R. et al. (Feb. 2004). "A subcutaneous delivery system for the extended release of leuprolide acetate for the treatment of prostate cancer," *Expert Opin Pharmacother* 5(2):447-457.

Radomsky, M.L. et al. (1993). "The Controlled Release of Ganirelix from the Atrigel™ Injectable Implant System," Proceed Intern *Symp Control Rel Bioact Mater* 20:458-459.

Rathbone, M.J. et al. (Aug. 1, 2002). "Modified release drug delivery in veterinary medicine," *Drug Discov Today* 7(15):823-829.

Ravivarapu, H.B. et al. (Feb. 28, 2000). "Sustained activity and release of leuprolide acetate from an in situ forming polymeric implant," *AAPS PharmSciTech* 1(1):E1.

Ravivarapu, H.B. et al. (Jun. 2000). "Sustained suppression of pituitary-gonadal axis with an injectable, in situ forming implant of leuprolide acetate," *J Pharm Sci* 89(6):732-741.

Ravivarapu, H.B. et al. (Jan. 25, 2000). "Parameters affecting the efficacy of a sustained release polymeric implant of leuprolide," *Int J Pharm* 194(2):181-191.

Schulman, C.C. (2005). "LHRH Agonists in Prostate Cancer Optimising Testosterone Control with Eligard®," *European Urology Supplements* 4:1-3.

Schwach-Abdellaoui, K. et al. (Jul. 2000). "Local delivery of antimicrobial agents for the treatment of periodontal diseases," *Eur J Pharm Biopharm* 50(1):83-99.

Sherman, J.M. et al. (1994). "Localized Delivery of Bupivacaine HCL from Astrigel™ Formulations for the Management of Postoperative Pain," *Pharmaceutical Research* 11(10), PDD7574, 2 pages.

Smith, R.W. et al. (2004). "A Study of Water Diffusion, in Both Radial and Axial Directions, into Biodegradable Monolithic Depots Using Ion Beam Analysis," *Polymer* 45:4893-4908.

Southard, G.L. et al. (Feb. 1998). "Subgingival controlled release of antimicrobial agents in the treatment of periodontal disease," *Int J Antimicrob Agents* 9(4):239-253.

Southard, G.L. et al. (Sep. 1998). "The drug delivery and biomaterial attributes of the Atrigel® technology in the treatment of periodontal disease," *Expert Opin Investig Drugs* 7(9):1483-1491.

Sundaram, S. et al. (2004). "Peptides: Nasal and Pulmonary Delivery of Deslorelin, a Peptide Drug," *American Pharmaceutical Review* 130-139.

Tipton, A.J. et al. (Oct. 1991). "A Biodegradable, Injectable Delivery System for NonSteroidal Anti-Flammatory Drugs," *Pharmaceutical Research* 8(10), PDD 7279, 2 pages.

Winzenburg, G. et al. (Jun. 23, 2004). "Biodegradable polymers and their potential use in parenteral veterinary drug delivery systems," *Adv Drug Deliv Rev* 56(10):1453-1466.

Wolff, E.D. et al. (1994). "Use of Bio-Beads SM-4 Adsorbent for Bioburden Testing of Atrigel™ Biodegradable Delivery System Containing 10% Doxycycline," ASM Las Vegas 1994, Abstracts, 3 pages.

Tserki, V. et al. (Feb. 2006). "Biodegradable aliphatic polyesters. Part II. Synthesis and characterization of chain extended poly(butylene succinate-co-butylene adipate)," *Polymer Degradation and Stability* 91(2):377-384.

(56) References Cited

OTHER PUBLICATIONS

Xia, Y. et al. (Jul. 18, 2002). "Uniform biodegradable microparticle systems for controlled release," *J Control Release* 82(1):137-147.
Astaneh, R. et al. (Jan. 2009). "Changes in morphology of in situ forming PLGA implant prepared by different polymer molecular weight and its effect on release behavior," *J Pharm Sci* 98(1):134-145.
Bartsch, W. et al. (1976). "Acute Toxicity in Various Solvents in the Mouse and Rat," *Arzneim-Forsch*, Drug Res 26:1581-1583.
Becci, P.J. et al. (1983). "Subchronic feeding study in beagle dogs of N-methylpyrrolidone," *J Appl Toxicol* 3(2):83-86.
Boongird, A. et al. (Jan. 2011). "Biocompatibility study of glycofurol in rat brains," *Exp Biol Med* 236(1):77-83.
Chu, F.M. et al. (Sep. 2002). "A clinical study of 22.5 mg. La-2550: A new subcutaneous depot delivery system for leuprolide acetate for the treatment of prostate cancer," *Journal of Urology* 168(3):1199-1203.
Contet C, Kieffer BL, Befort K. Mu opioid receptor: a gateway to drug addiction. *Curr Opin Neurobiol* 14:370-378, 2004.
Crawford, E.D. et al. (Feb. 2006). "A 12-month clinical study of LA-2585 (45.0 mg): a new 6-month subcutaneous delivery system for leuprolide acetate for the treatment of prostate cancer," *Journal of Urology* 175(2):533-536.
Dadey, E.J. (2008). The Atrigel Drug Delivery System. In: Rathbone et al Eds, Modified-Release Drug Delivery Technology, $2^{nd}$ Ed., New York, pp. 183-190.
Domb, A.J. et al. (1989). "Solid-State and Solution Stability of Poly(anhydrides) and Poly(esters)," *Macromolecules* 22(5):2117-2122.
Eliaz, R.E. et al. (Dec. 2000). "Delivery of soluble tumor necrosis factor receptor from in-situ forming PLGA implants: in-vivo," *Pharm Research* 17(12):1546-1550.
FDA Document K982865 (1998). Atrix Laboratories, Inc. 13 pages.
FDA Document K994137 (2000). Atrix Laboratories, Inc. 9 pages.
Frost, J.J., Wagner, H.N. Jr., Dannals, R.F., Ravert, H.T., Links, J.M., Wilson, A.A., Burns, H.D., Wong, D.F., McPherson, R.W., Rosenbaum, A.E., Kuhar, M.J. & Snyder, S.H. (1985). Imaging opiate receptors in the human brain by positron tomography. *J Comp Assist Tomogr*, 9, 231-236.
Greenwald MK, Johanson CE, Moody DE, Woods JH, Kilbourn MR, Koeppe RA, Schuster CR, Zubieta JK (2003) *Neuropsychopharmacology* 28: 2000-2009.
Greenwald MK, Johanson CE, Bueller J, Chang Y, Moody DE, Kilbourn MR, Koeppe RA, Zubieta JK (2007) Buprenorphine duration of action: Mu-opioid receptor availability, pharmacokinetic and behavioral indices. *Biological Psychiatry* 61: 101-110.
Hempel, G. et al. (May 1, 2007). "Cytotoxicity of dimethylacetamide and pharmacokinetics in children receiving intravenous busulfan," *J Clin Oncol* 25(13):1772-1778.
Johnson, O.L. et al. (Jun. 1997). "The stabilization and encapsulation of human growth hormone into biodegradable microspheres," Pharm res 14(6):730-735.
Lee, K.P. et al. (Aug. 1987). "Toxicity of N-methyl-2-pyrrolidone (NMP): teratogenic, subchronic, and two-year inhalation studies," *Fundam Appl Toxicol* 9(2):222-235.
Lester PA, Traynor JR. Comparison of the in vitro efficacy of mu, delta, kappa and ORL1 receptor agonists and non-selective opioid agonists in dog brain membranes. *Brain Res*. 2006;1073-1074:290-296.
Lewis JW., Buprenorphine. Drug Alcohol Depend. 1985; 14:363-372.
Li, M. et al. (Nov. 2003). "A novel, non-prostanoid EP2 receptor-selective prostaglandin E2 agonist stimulates local bone formation and enhances fracture healing," *Bone Miner Res* 18(11):2033-2042.
Liao, C-L. et al. (2008). "In vitro skin permeation of buprenorphine transdermal patch," *Journal of Food and Drug Analysis* 16(6):8-15.
Lindhardt et al, "Intranasal Absorption of Buprenorphine—in vivo biovavailability study in sheep." Int. J. Pharm., 205(1-2):159-163 (2000).

Ling W, Wesson DR, Charuvastra C, Klett CJ. A controlled trial comparing buprenorphine and methadone maintenance in opioid dependence. *Arch. Gen. Psychiatry*. 1996; 53:401-407.
Ling W, Charuvastra C, Collins JF, Batki S, Brown LS, Jr, Kintaudi P, Wesson DR, McNicholas L, Tusel DJ, Malkerneker U, Renner JA, Jr, Santos E, Casadonte P, Fye C, Stine S, Wang RI, Segal D. Buprenorphine maintenance treatment of opiate dependence: a multicenter, randomized clinical trial. *Addiction*. 1998; 93:475-486.
Lutfy K, Cowan A. Buprenorphine: a unique drug with complex pharmacology. *Curr. Neuropharmacol*. 2004; 2:395-402.
Makadia, H.K. et al. (Sep. 1, 2011, e-published Aug. 26, 2011). "Poly Lactic-co-Glycolic Acid (PLGA) as Biodegradable Controlled Drug Delivery Carrier," *Polymers* 3(3):1377-1397.
Matthes HW, Maldonado R, Simonin F, Valverde O, Slowe S, Kitchen I, Befort K, Dierich A, Le Meur M, Dolle P, Tzavara E, Hanoune J, Roques BP, Kieffer BL. Loss of morphine-induced analgesia, reward effect and withdrawal symptoms in mice lacking the mu-opioid-receptor gene. *Nature* 1996; 383:819-823.
Miller, R.A. et al. (Sep. 1977). "Degradation rates of oral resorbable implants (polylactates and polyglycolates): rate modification with changes in PLA/PGA copolymer ratios," *Biomed Mater Res* 11(5):711-719.
Paralkar, V.M. et al. (May 27, 2003, e-published May 14, 2003). "An EP2 receptor-selective prostaglandin E2 agonist induces bone healing," *PNAS USA* 100(11):6736-6740.
Parent, M. et al. (Nov. 28, 2013, e-published Sep. 1, 2013). "PLGA in situ implants formed by phase inversion: critical physicochemical parameters to modulate drug release," *J Control Release* 172(1):292-304.
Patel, R.B. et al. (Nov. 1, 2010, e-published Aug. 20, 2010). "Effect of injection site on in situ implant formation and drug release in vivo," *J Control Release* 147(3):350-358.
Perez-Merreno, R. (Nov. 2002). "A six-month, open-label study assessing a new formulation of leuprolide 7.5 mg for suppression of testosterone in patients with prostate cancer," *Clinical Therapuetics* 24(11):1902-1914.
Schoenhammer, K. et al. (Apr. 17, 2009, e-published Dec. 24, 2008). "Injectable in situ forming depot systems: PEG-DAE as novel solvent for improved PLGA storage stability," *Int J. Pharm* 371(1-2):33-39.
Schoenhammer, K. et al. (Dec. 2009, e-published Oct. 1, 2009). "Poly(ethyleneglycol) 500 dimethylether as novel solvent for injectable in situ forming depots," *Pharm Res* 26(12):2568-2577.
Sigmon et al, "An injection depot formulation of buprenorphine: extended biodelivery and effects," Addiction, 101:420-432 (2006).
Sinha, V.R. et al. (Jun. 18, 2004). "Poly-epsilon-caprolactone microspheres and nanospheres: an overview," *Int J. Pharm* 278(1):1-23.
Sobel et al, "Open-label trial of an injection depot formulation of buprenorphine in opioid detoxification," Drug and Alcohol Dependence, 73:11-22 (2004).
Swanson, B.N. (Jan.-Jun. 1985). "Medical use of dimethyl sulfoxide (DMSO)," *Rev Clin Basic Pharm* 5(1-2):1-33.
Titeler, M., Lyon, R.A., Kuhar, M.J., Frost, J.J., Dannals, R.F., Leonhardt, S., Bullock, A., Rydelek, L.T., Price, D.L. & Struble, R.G. (1989). Mu opiate receptors are selectively labeled by [3H]-carfentanil in human and rat brain. *Eur J Pharmacol*, 167, 221-228.
Tunn, U.W. (Jul. 29, 2011). "A 6-month depot formulation of leuprolide acetate is safe and effective in daily clinical practice: a non-interventional prospective study in 1273 patients," *BMC Urology* 11:15.
Veilleux JC, Colvin PJ, Anderson J, York C, Heinz AJ. A review of opioid dependence treatment: pharmacological and psychosocial interventions to treat opioid addiction. *Clin Psychol Rev* 2010; 30: 155-166.
World Health Organization (2001). N-Methyl-2-Pyrrolidone, Concise International Chemical Assessment Document 35, 39 pages.
Zhu, G. et al. (2000). "Stabilization of proteins encapsulated in cylindrical poly(lactide-co-glycolide) implants: mechanism of stabilization by basic additives," *Pharm Res* 17(3):351-357.
International Preliminary report on Patentability dated Jun. 29, 2016 for PCT Application No. PCT/GB2015/050676, filed Mar. 9, 2015, 18 pages.

(56) References Cited

OTHER PUBLICATIONS

International Search Report dated Jun. 11, 2015 for PCT Application No. PCT/GB2015/050676, filed Mar. 9, 2015, 6 pages.
Written Opinion dated Jun. 11, 2015 for PCT Application No. PCT/GB2015/050676, filed Mar. 9, 2015, 6 pages.
International Search Report and Written Opinion dated May 10, 2012 for priority application PCT/GB2011/051058, 10 pages.
International Preliminary Report on Patentability dated Dec. 20, 2012 for priority application PCT/GB2011/051058, 7 pages.
Search Report dated Oct. 6, 2010 for priority application GB1009546. 1, 2 pages.

SUSTAINED-RELEASE BUPRENORPHINE SOLUTIONS

RELATED APPLICATIONS

This application is a continuation of U.S. application Ser. No. 15/125,052 filed Sep. 9, 2016, issued as U.S. Pat. No. 10,022,367 which is a Section 371 US National Phase of International Application No. PCT/GB2015/050676 filed Sep. 9, 2015, which claims priority to United Kingdom Application No. 1404139.6 filed Mar. 10, 2014, the disclosures of which are incorporated by reference herein in their entirety.

FIELD

This disclosure relates to sustained-release pharmaceutical formulations comprising a solution of an opioid and a biocompatible organic solvent. The pharmaceutical formulations are capable of providing sustained release of an opioid for a period of at least one month after a single injection into a patient. The pharmaceutical formulations are useful for the treatment of pain and opioid dependence.

BACKGROUND

Buprenorphine (also known as (2S)-2-[(−)-(5R,6R,7R,14S)-9a-cyclo-propyl-methyl-4,5-epoxy-6,14-ethano-3-hydroxy-6-methoxymorphinan-7-yl]-3,3-di-methylbutan-2-ol and marketed under the trade names SUBUTEX® (buprenorphine by Indivior PLC) and SUBOXONE® (buprenorphine/naloxone by Indivior PLC) for the treatment of opioid dependence. These products are in tablet and film formulations and are intended to deliver daily therapeutic levels of buprenorphine and are taken either buccally or sublingually. However, there are often issues with diversion in patients with an opioid dependence problem. There is a need therefore for a longer term, non-divertible method of administering buprenorphine which delivers a constant and effective dose of buprenorphine to the patient over a period of a month or longer, and which does not result in an accumulation of buprenorphine in the patient's metabolism.

Various sustained release methods are employed in the pharmaceutical industry, for example, a non-degradable buprenorphine implant, PROBUPHINE® (Titan Pharmaceuticals), has been shown to release buprenorphine for six months once implanted in patients. Although the implant may be efficacious to treat opioid dependence (Ling et al, JAMA, 304(14):1576-83 (2010)), it requires surgical procedure for placement in the patent and a second surgical procedure to remove the empty reservoir from the patient.

A biodegradable buprenorphine delivery system that can be easily injected and requires no surgical removal has also been investigated. Sigmon et al, Addiction, 101:420-432 (2006) reported a biodegradable polymer microcapsule depot system that was able to sustain plasma buprenorphine levels for at least 4 weeks after a single intramuscular injection. Such microcapsule systems, however, can only be produced by a complex manufacture process.

A flowable biodegradable liquid system is disclosed in WO 2011/154724. This system utilizes a biodegradable polymer, a biocompatible solvent, and buprenorphine, all solubilized as an injectable liquid that can slowly release buprenorphine for one month or longer. This system forms a solid implant in situ following injection.

US Publication No. 2013/0190341 discloses a lipid-based precursor formulation that utilizes phosphatidyl choline and glycerol dioleate to form a liquid crystal phase to control the release of buprenorphine. In order to make the formulation injectable, ethanol was added to dissolve all the components, including buprenorphine, to form a solution. Such a solution may provide buprenorphine plasma levels for up to 2 weeks after a single subcutaneous injection.

WO 2007/103185 discloses rapid-release buprenorphine suspensions in various solvent systems that form drug depots at the injection sites. The solvent systems include aqueous solutions and water immiscible sesame oil as well as water miscible organic solvents such as citric acid esters and polyethylene glycol. The slowest release formulation exemplified in the application released 53.97% buprenorphine in 6 days in mice, and achieved an analgesic effect for 4 to 5 days.

WO 2011/154725 describes buprenorphine aqueous suspensions containing surfactants with high buprenorphine drug loadings of 10% or more. Those suspensions appear to continuously release buprenorphine for about a month in rats and 14 to 20 days in dogs after a single subcutaneous or intramuscular injection.

Although all the systems described above allegedly provide sustained release of buprenorphine, there is still a need to develop better sustained release formulations of buprenorphine that are easy to prepare and easy to inject, with better release kinetics, and that can last at least a month or longer.

SUMMARY

The disclosure provides non-polymeric, opioid formulations that are capable of delivering a therapeutically effective amount of an opioid to a patient for at least a month. The formulations comprise a solution of (i) a therapeutically effective amount of an opioid; (ii) a biocompatible organic solvent; and (iii) optionally a glycol. The opioid is preferably an opioid agonist, such as buprenorphine, morphine, hydromorphone, fentanyl, oxycodone, hydrocodone, meperidine, codeine, methadone, diphenoxylate, or propoxyphene. The biocompatible organic solvent can be any known in the art, such as N-methyl-2-pyrrolidone, dimethyl acetamide, dimethyl sulfoxide, or a combination of two or more thereof. The glycol can be any known in the art, such as a polyethylene glycol, a propylene glycol, or a combination thereof.

According to one aspect of the invention there is provided a pharmaceutical solution comprising, consisting essentially of, or consisting of: (i) at least 5 wt % buprenorphine in the form of a free base or a pharmaceutically acceptable salt, and (ii) a biocompatible organic solvent selected from the group consisting of N-methyl-2-pyrrolidone, dimethyl acetamide, dimethyl sulfoxide, and a combination of two or more thereof; wherein the pharmaceutical solution does not comprise a biodegradable polymer. In one embodiment the solution comprises at least 8 wt % buprenorphine, for example at least 9 wt % or at least 10 wt %.

In one embodiment there is provided a composition comprising a solution of 5-55 wt % of buprenorphine dissolved in a biocompatible organic solvent selected from N-methyl-2-pyrrolidone (NMP), dimethyl acetamide (DMAC), or dimethyl sulfoxide (DMSO) wherein the composition does not comprise any biodegradable polymer.

In one embodiment, the disclosure provides formulations comprising, consisting essentially of, or consisting of: (i) 10 wt % to 55 wt % buprenorphine in the form of a free base or a pharmaceutically acceptable salt; (ii) a biocompatible organic solvent selected from the group consisting of N-methyl-2-pyrrolidone, dimethyl acetamide, dimethyl sulfoxide, and a combination of two or more thereof; (iii) optionally a glycol, for example a glycol selected from the group consisting of a polyethylene glycol, a propylene glycol, or a combination thereof; (iv) optionally water; and (v) optionally an antioxidant; wherein the formulation does not comprise a biodegradable polymer. When a glycol is present, the weight ratio of (i):(ii):(iii) may be from 1:3:7 to 1:0.5:0.1. Optionally the weight ratio of (i):(ii):(iii) may be from 1:2.7:6.3 to 1:0.74:0.08. The formulations may be used to treat opioid dependence or pain.

These and other aspects of the invention are described in more detail herein.

BRIEF DESCRIPTION OF THE FIGURES

In FIG. 1 the open square and open circle data points refer to the % buprenorphine released and the solid circle and solid square data points refer to the buprenorphine plasma levels.

DETAILED DESCRIPTION

Figure 1:
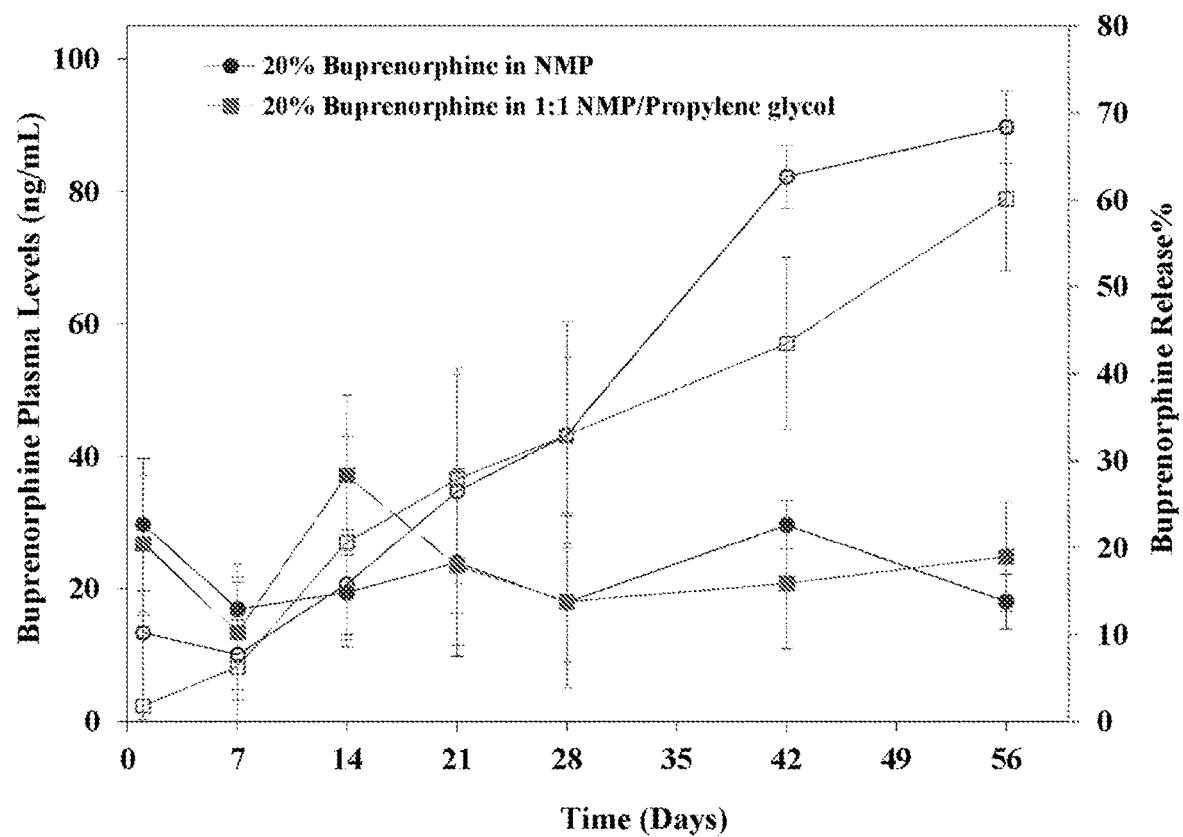
FIG. 1 illustrates buprenorphine release and plasma levels after subcutaneous injection of buprenorphine solutions in rats.

Surprisingly, it has been found that a solution of an opioid, such as buprenorphine, at a relatively high concentration in a biocompatible organic solvent, such as N-methyl-2-pyrrolidone (NMP), dimethyl acetamide (DMAC), or dimethyl sulfoxide (DMSO), without any release modifying agents, such as biodegradable or non-degradable polymers, and without any complexing agents, such as cyclodextrin, can provide constant and prolonged opioid release for at least one month after a single subcutaneous injection in animals.

One aspect of the invention provides a pharmaceutical solution comprising: (i) at least 5 wt % buprenorphine in the form of a free base or a pharmaceutically acceptable salt, and (ii) a biocompatible organic solvent selected from the group consisting of N-methyl-2-pyrrolidone, dimethyl acetamide, dimethyl sulfoxide, and a combination of two or more thereof, wherein the pharmaceutical solution does not comprise a biodegradable polymer.

The solution may comprise at least 6 wt %, at least 7 wt %, at least 8 wt %, at least 9 wt %, at or least 10 wt % buprenorphine in the form of a free base or a pharmaceutically acceptable salt. Solutions comprising a high concentration (for example, at least 5 wt %) of buprenorphine in the biocompatible organic solvent exhibit a low initial burst following subcutaneous administration of the solution to a subject. In particular solutions comprising at least 8 wt %, for example at least 9 wt %, or particularly, at least 10 wt % buprenorphine have been found to exhibit a low initial burst following subcutaneous administration of the solution. By "initial burst" is meant the initial release of buprenorphine from the solution shortly after subcutaneous administration of the solution, for example 24 hours after administration of the solution. The initial burst may be determined as illustrated in the examples. For example, the initial burst may be estimated from PK data by measuring the ratio of the area under the curve (AUC) in the initial 24 hours: the total AUC over the duration of release from the solution (i.e $AUC_{0-\infty}$ (or an approximation thereof, for example $AUC_{0-28\ days}$, $AUC_{0-122\ days}$ or $AUC_{0-178\ days}$) in blood plasma. Suitably the initial burst is less than 10%, for example less than 5%, less than 4.5%, less than 4%, less than 3.5% or less than 3% by weight of the buprenorphine administered to a subject is released from the solution in the 24 hours following subcutaneous administration of the solution. For example, the initial burst may be from about 1% to about 10%, from about 1.5% to about 6%, from about 2% to about 5%, from about 1.5% to about 4.5% by weight of buprenorphine is released in the first 24 hours after subcutaneous administration of the solution. The initial burst is minimised when the solution comprises a solution of buprenorphine in the free base form.

As will be recognized, the upper limit of the buprenorphine which may be present in the solution is limited by the solubility of the buprenorphine in the particular biocompatible solvent(s), and other optional components of the solution, for example the glycol and/or water. As illustrated in the Examples, the free base form of the buprenorphine has a higher solubility in the biocompatible organic solvent(s) than the hydrochloride salt of buprenorphine. Accordingly, in particular embodiments the solution comprises a solution of buprenorphine in the form of the free base dissolved in biocompatible solvent(s), and other optional components of the solution. Additionally, temperature will affect the upper solubility limit of buprenorphine dissolved in the solution. In some embodiments the upper limit of buprenorphine present in the solution is, for example, the solubility limit at room temperature (20 to 22° C., particularly at about 21° C.). The high solubility of the free base form of buprenorphine in the biocompatible organic solvent(s) enables high concentration buprenorphine solutions to be prepared. A high concentration of buprenorphine in the solution enables a high dose of buprenorphine to be administered in a relatively small injection volume.

When the buprenorphine is in the free base form the solution suitably comprises for example, up to 15 wt %, up to 20 wt %, up to 25 wt %, up to 30 wt %, up to 35 wt %, up to 40 wt %, up to 45 wt %, up to 50 wt %, up to 55 wt % or up to 60 wt % of buprenorphine.

When the buprenorphine is in the form of a salt, for example a hydrochloride salt of buprenorphine, the solution suitably comprises, for example up to 11 wt %, up to 12 wt %, up to 13 wt %, up to 14 wt %, up to 15 wt %, up to 16 wt %, up to 17 wt %, up to 18 wt % or up to 19 wt % of the buprenorphine.

One aspect of the invention provides a composition comprising a solution of 5 wt % to 55 wt % buprenorphine dissolved in a biocompatible organic solvent, wherein the composition does not comprise a biodegradable polymer. In one embodiment, the biocompatible solvent is NMP, DMAC, DMSO, or a combination of two or more thereof. In one embodiment, the solution can comprise from 10 wt % to 55 wt % buprenorphine. In one embodiment, the solution can comprise from 10 wt % to 50 wt % buprenorphine. In one embodiment, the solution can comprise 15 wt % to 50 wt % buprenorphine. In one embodiment, the solution can comprise 20 wt % to 45 wt % buprenorphine. In one embodiment, the solution can comprise from 20 wt % to 40 wt % buprenorphine. In one embodiment, the solution can comprise 25 wt % to 45 wt % buprenorphine. In one embodiment, the solution can comprise 30 wt % to 40 wt % buprenorphine. In another embodiment the solution comprises about 20 wt %, about 25 wt %, about 30 wt %, about 35 wt %, about 40 wt %, about 45 wt %, about 50 wt % or about 55 wt % buprenorphine. The buprenorphine can be present in the form of a free base (unprotonated) or a pharmaceutically acceptable salt (e.g., HCl). In one embodiment, the buprenorphine is in the form of a free base. In another embodiment the buprenorphine is in the form of a pharmaceutically acceptable salt (e.g., HCl).

In certain embodiments the biocompatible organic solvent is N-methyl-2-pyrrolidone.

In certain embodiments the biocompatible organic solvent is dimethyl acetamide.

In certain embodiments the biocompatible organic solvent is dimethyl sulfoxide.

With respect to dosage, the solution can comprise up to 500 mg buprenorphine, for example from 1 mg to 500 mg of buprenorphine. In one embodiment, the solution can comprise from 10 mg to 350 mg of buprenorphine. In one embodiment, the solution can comprise from 150 mg to 300 mg of buprenorphine. In one embodiment, the solution can comprise from 10 mg to 50 mg buprenorphine.

In other embodiments, the composition can comprise up to 500 mg buprenorphine in a 1 cc volume of injection, for example from 1 mg to 500 mg buprenorphine in a 1 cc volume of injection. The composition can comprise from up to 350 mg buprenorphine in a 1 cc volume of injection, for example from 10 mg to 350 mg buprenorphine in a 1 cc volume of injection. The composition can comprise 150 mg to 300 mg of buprenorphine in 1 cc or less volume of injection. The composition can comprise 10 mg to 50 mg buprenorphine in 0.2 cc or less volume of injection.

The solution can optionally further comprise up to 10% by weight water, for example up to 8%, up to 6%, up to 4% or up to 2% by weight water. Suitably the solution may comprise from about 0.01% by weight to about 10% by weight of water. The addition of water may reduce local irritations caused by the biocompatible organic solvent. Solutions comprising, for example, up to 10% by weight water are suitable when the solution is a solution of the free base form of buprenorphine.

When the solution is a solution of a salt of buprenorphine in the biocompatible solvent(s) and optional other components, the solution may optionally contain higher amounts of water, for example the solution may further comprise up to 20% by weight of water.

Accordingly, the solutions comprising a solution of a salt of buprenorphine, for example a HCl salt, may further comprise up to 18%, up to 16%, up to 14% or up to 12%, up to 10% up to 8%, up to 6%, up to 4% or up to 2% by weight water.

In another embodiment the solution does not comprise water.

In other embodiments, the solution may further comprise a glycol up to 70% by weight, for example in an amount from 5% to 70% by weight of the solvent mixture. The glycol may also reduce local irritations of the biocompatible organic solvent (for example NMP). In other embodiments, the glycol can be present in an amount from 10% to 60% by weight of the solvent mixture. In other embodiments, the glycol can be present in an amount from 15% to 50% by weight of the solvent mixture. In other embodiments, the glycol can be present in an amount from 20% to 60% by weight of the solvent mixture; or from 20% to 50% by weight of the solvent mixture. In other embodiments, the glycol can be present in an amount from 20% to 40% by weight of the solvent mixture. In other embodiments, the glycol can be present in an amount from 20% to 30% by weight of the solvent mixture. It is to be understood that references to the "% glycol by weight of the solvent mixture" means the % by weight of the glycol present in the mixture of the biocompatible organic solvent(s) (ii), and the glycol present in the solution.

In one embodiment, the solvent mixture comprises from 90 wt % to 50 wt % of a biocompatible organic solvent and from 10 wt % to 50 wt % of a glycol. In one embodiment, the solvent mixture comprises from 80 wt % to 50 wt % of a biocompatible organic solvent and from 20 wt % to 50 wt % of a glycol. In one embodiment, the solvent mixture comprises from 70 wt % to 50 wt % of a biocompatible organic solvent and from 30 wt % to 50 wt % of a glycol.

The glycol can be polyethylene glycol (PEG), propylene glycol, or a combination thereof. In one embodiment, the glycol is a polyethylene glycol having an average molecular weight from about 100 to about 1,000. In one embodiment, the glycol is a polyethylene glycol having an average molecular weight from about 100 to about 800. In one embodiment, the glycol is a polyethylene glycol having an average molecular weight from about 200 to about 500. In one embodiment, the glycol is a polyethylene glycol having an average molecular weight from about 250 to about 450. In one embodiment, the polyethylene glycol is PEG300, PEG 400, or a combination thereof, both of which are commercially available from, e.g., Sigma-Aldrich or the Dow Chemical Company. In one embodiment, the glycol is PEG300, PEG400, propylene glycol, or a combination of two or more thereof. In one embodiment, the glycol is PEG300. In one embodiment, the glycol is PEG400. In one embodiment, the glycol is a combination of PEG300 and PEG400. In one embodiment, the glycol is propylene glycol.

The term "PEG300" refers to polyethylene glycol having an average molecular weight from about 280 to about 320. The term "PEG400" refers to polyethylene glycol having an average molecular weight from about 380 to about 420. The term "propylene glycol" refers to the compound $CH_3CH(OH)CH_2OH$ having a molecular weight of about 76.

The ratio of biocompatible organic solvent to glycol can be from 0.4:1 to 4:1. In one embodiment, the ratio is from 0.65:1 to 2.5:1. In one embodiment, the ratio is from 1:1 to 1.5:1.

The ratio of buprenorphine to glycol can be from 0.15:1 to 5:1. In one embodiment, the ratio is from 0.4:1 to 3.5:1. In one embodiment, the ratio is from 0.5:1 to 1:1.

In one embodiment, the composition comprises buprenorphine, a biocompatible organic solvent selected from one or more of NMP, DMAC, and DMSO; and a glycol selected from polyethylene glycol (e.g., PEG300, PEG400), propylene glycol or a combination thereof; where the ratio of biocompatible organic solvent to glycol is from 1:3:7 to 1:0.5:0.1. In one embodiment, the ratio of buprenorphine to biocompatible organic solvent to glycol is from 1:2.7:6.3 to 1:0.74:0.08. In one embodiment, the ratio of buprenorphine to biocompatible organic solvent to glycol is from 1:2:2 to 1:1:0.4. In other embodiments, the ratio of buprenorphine to biocompatible organic solvent to glycol is 1:2.7:6.3, 1:1.5:1.5, 1:1.4:0.93, 1:1.05:0.45, or 1:0.8:0.2. In another embodiment, the ratio of buprenorphine to biocompatible organic solvent to glycol is 1:0.74:0.08.

In any of the embodiments described herein relating to solutions comprising biocompatible organic solvent and a glycol, the organic solvent may be for example NMP and the glycol may be for example propylene glycol.

In any of the embodiments described herein relating to solutions comprising biocompatible organic solvent and a glycol, the organic solvent may be for example NMP and the glycol may be for example PEG 300.

In any of the embodiments described herein relating to solutions comprising biocompatible organic solvent and a glycol, the organic solvent may be for example NMP and the glycol may be for example PEG 400.

Suitably the only solvent(s) present in the solution are the biocompatible organic solvent(s); optionally a glycol and optionally water. Accordingly in one embodiment the solution does not contain any organic solvents other than N-methyl-2-pyrrolidone, dimethyl acetamide, dimethyl sulfoxide, or a glycol, or a combination of two or more thereof. In another embodiment the solution consists of the buprenorphine dissolved in N-methyl-2-pyrrolidone, dimethyl acetamide, dimethyl sulfoxide, optionally a glycol and optionally water, or a combination of two or more thereof. In another embodiment the solution consists of the buprenorphine dissolved in N-methyl-2-pyrrolidone, dimethyl acetamide, dimethyl sulfoxide and optionally a glycol, or a combination of two or more thereof. In another embodiment the solution consists of the buprenorphine dissolved in N-methyl-2-pyrrolidone, dimethyl acetamide, or dimethyl sulfoxide, or a combination of two or more thereof. In these embodiments the concentration of buprenorphine, solvents(s), optional glycol and optional water, may be any of the values disclosed herein.

The compositions described herein can optionally further comprise one or more pharmaceutically acceptable antioxidants. The antioxidant may be ascorbic acid, vitamin E, butylated hydroxytoluene (BHT), butylated hydroxyanisole (BHA), ethylenediaminetetraacetic acid (EDTA), or a combination thereof. In one embodiment, the antioxidant is ascorbic acid, vitamin E, BHT, BH-A, or a combination thereof. The antioxidant may be present in an amount from about 0.01 wt % to about 10 wt %, or from about 0.1 wt % to about 5 wt %, or from about 0.1 wt % to about 3 wt %. The antioxidant may enhance the stability of buprenorphine.

In one embodiment, the composition can consist essentially of buprenorphine, NMP, and PEG400, which are present in a ratio from 1:3:7 to 1:0.5:0.1. In one embodiment, the ratio can be from 1:2.7:6.3 to 1:0.74:0.08. In one embodiment, the ratio can be from 1:2:2 to 1:1:0.4. In other embodiments, the ratio can be 1:2.7:6.3, 1:1.5:1.5, 1:1.4:0.93, 1:1.05:0.45, 1:0.8:0.2 or 1:0.74:0.08.

In one embodiment, the composition can consist of buprenorphine, NMP, and PEG400, which are present in a ratio of from 1:3:7 to 1:0.5:0.1. In one embodiment, the ratio can be from 1:2.7:6.3 to 1:0.74:0.08. In other embodiments, the compounds are present in a ratio of from 1:2:2 to 1:1:0.4. In other embodiments, the ratio is 1:2.7:6.3, 1:1.5:1.5, 1:1.4:0.93, 1:1.05:0.45, or 1:0.8:0.2 or 1:0.74:0.08.

In one embodiment, the composition can consist essentially of buprenorphine, NMP, and PEG300, which are present in a ratio from 1:3:7 to 1:0.5:0.1. In one embodiment, the ratio can be from 1:2.7:6.3 to 1:0.74:0.08. In one embodiment, the ratio can be from 1:2:2 to 1:1:0.4. In other embodiments, the ratio can be 1:2.7:6.3, 1:1.5:1.5, 1:1.4:0.93, 1:1.05:0.45, 1:0.8:0.2 or 1:0.74:0.08.

In one embodiment, the composition can consist of buprenorphine, NMP, and PEG300, which are present in a ratio of from 1:3:7 to 1:0.5:0.1. In one embodiment, the ratio can be from 1:2.7:6.3 to 1:0.74:0.08. In other embodiments, the compounds are present in a ratio of from 1:2:2 to 1:1:0.4. In other embodiments, the ratio is 1:2.7:6.3, 1:1.5:1.5, 1:1.4:0.93, 1:1.05:0.45, 1:0.8:0.2 or 1:0.74:0.08.

In other embodiments, the composition can consist of about 40% buprenorphine in NMP. In other embodiments, the composition can consist of about 15% to about 35% buprenorphine in a solution containing NMP and PEG400, where the NMP and PEG400 are present in a ratio ranging from 40:60 to 70:30, preferably in a ratio from 50:50 to 60:40. In one embodiment, the composition can consist of about 30% buprenorphine in a 60:40 NMP/PEG400 solution. In another embodiment, the composition can consist of about 20% buprenorphine in a 50:50 NMP/PEG400 solution. In other embodiments, the composition can consist of about 15% to about 35% buprenorphine in a solution containing NMP and PEG300 in a ratio ranging from 40:60 to 70:30, preferably in a ratio from 50:50 to 60:40. In one embodiment, the composition can consist of about 20% buprenorphine in a 50:50 NMP/PEG300 solution. In another embodiment, the composition can consist of about 30% buprenorphine in a 60:40 NMP/PEG300 solution.

In other embodiments the composition can consist of about 300 mg of buprenorphine in about 450 mg NMP. In other embodiments, the composition can consist of about 300 mg of buprenorphine in about 700 mg of a 60:40 NMP/PEG400 solution. In other embodiments, the composition can consist of about 150 mg of buprenorphine in about 600 mg of a 50:50 NMP/PEG400 solution. In other embodiments, the composition can consist of about 20 mg of buprenorphine in about 80 mg of a 50:50 NMP/PEG400 solution. In other embodiments, the composition can consist of about 50 mg of buprenorphine in about 117 mg of a 60:40 NMP/PEG400 solution.

Unless specified otherwise, reference herein to a % of a particular component is a reference to a % by weight.

According to a further aspect of the invention there is provided a composition described herein for use as a medicament.

According to a further aspect of the invention there is provided a composition described herein for use in the treatment of opioid dependence or pain.

According to a further aspect of the invention there is provided the use of a composition described herein in the manufacture of a medicament for the treatment of opioid dependence or pain.

According to another aspect of the invention, there is provided a method of treating a patient for opioid dependence or pain comprising subcutaneously administering to the patient a therapeutically effective amount of any of the compositions described herein.

According to another aspect of the invention there is provided a composition as described herein for use in treating a patient for opioid dependence or pain, wherein the composition is administered to the patient subcutaneously.

According to another aspect of the invention there is provided the use of a composition as described herein for the manufacture of a medicament for treating a patient for opioid dependence or pain, wherein the composition is administered to the patient subcutaneously.

In one embodiment the compositions for use, use of the compositions and methods described herein are for the treatment of pain.

In one embodiment the compositions for use, use of the compositions and methods described herein are for the treatment of opioid dependence.

Preferably, the compositions for use, use of the compositions and methods described herein provide treatment for opioid dependence or pain by subcutaneously administering a therapeutically effective amount of any of the compositions described herein once per month. The term "month" refers to a period of time from 28 days to 31 days. In one embodiment, a month is 30 days. In other embodiments, the compositions are subcutaneously administered to the patient once every three months.

Typically, the "therapeutically effective amount" refers to buprenorphine in an amount from about 0.10 milligrams (mg) to about 10 mg per day. The methods of administration can provide a therapeutically effective level of buprenorphine within about one day after administration of the composition. The compositions described herein may provide therapeutically effective levels of buprenorphine for about one month to about three months after administration.

Preparation of Composition

The present invention provides a method of manufacturing a composition, suitably as defined herein. The method suitably comprises mixing together, in any particular order deemed appropriate, any relevant components required to form a composition as defined herein. The skilled person may refer to the Examples or techniques well known in the art for forming pharmaceutical solution compositions. Different embodiments will suitably require different combinations of components to be mixed, potentially in different amounts. The skilled person can readily deduce such combinations and amounts by reference to the foregoing disclosure relating to the composition.

Suitably the method involves mixing together the relevant components, suitably so that all of the components are (substantially or entirely) dissolved in the biocompatible organic solvent. Suitably the solution is prepared at room temperature. Alternatively the mixture may be heated gently to for example 30 to 40° C. to aid dissolution of the buprenorphine in the biocompatible organic solvent(s) and other components.

The method may involve first preparing a one or more pre-mixtures (or pre-solutions) of each, some or all components, before said pre-mixture(s) or pre-solution(s) are then mixed together, optionally along with any components not provided as a pre-mixture or pre-solution to ultimately form the solution.

The buprenorphine present in the solutions described herein is dissolved in the solution. Preferably all of the buprenorphine is dissolved in the solution. However, in some embodiments the solution may comprise small amounts of buprenorphine which is not dissolved, for example less than 5 wt %, less than 1 wt % or less than 0.1 wt % may be present as solids, although this is not preferred. Accordingly, if the solution contains solid buprenorphine the solids are preferably removed prior to use of the solution by for example filtration.

The final composition may be filtered, suitably to remove particulate matter. Suitably filtration is through filters sized at or below 1 mm, suitably at 0.22 mm. Suitably, filtration is through either PES filters or PVDF filters, suitably with 0.22 mm PES filters.

The solutions described herein are preferably prepared as a sterile solution. Methods for preparing sterile pharmaceutical solutions are well known and include for example preparing the solution from sterile components under aseptic processing conditions or by sterile filtration of the solution. Accordingly in a further embodiment there is provided any of the solutions described herein in a sterile form. The solutions are suitably pyrogen free. Generally a pyrogen free solution may be prepared using pyrogen-free starting materials and pyrogen free reaction vessels/processing equipment. Accordingly, particular solutions are those which are sterile and pyrogen free.

Package or Medical Device

The compositions of the invention may be incorporated into a package or medical device, for example, comprising a sterile container pre-filled or to be filled with a composition as defined herein. The present invention therefore provides a package or medical device, comprising a sterile container pre-filled or configured for filling with a composition as defined herein. The sterile container is suitably pyrogen-free.

The sterile container is suitably selected from a syringe, dispenser, cartridge, vial, ampoule, bottle or self-injection pen.

In some embodiments, the device or package may be filled immediately prior to use with the composition. In some embodiments, the composition may be provided within the device or package, for example as a pre-filled syringe.

Kit of Parts

The present invention provides a kit of parts comprising a medical device (without the composition incorporated therein), a composition as defined herein (optionally contained in a separate package or container), and optionally a set of instructions with directions regarding the administration (e.g. subcutaneous administration of the composition. The user may then fill the medical device with the composition (which may be provided in a vial or ampoule or such like) prior to administration The compositions described herein are suitably prepared as a medicinal product comprising a container and the composition.

EXAMPLES

The following examples are for illustrative purposes and are not intended to limit the scope of the disclosure.

All rat preclinical studies were conducted in male Sprague-Dawley rats. Five rats per Test Article per time point were injected subcutaneously under full anesthesia in the dorsal thoracic (DT) region with approximately 100 mg of the Test Article, described below.

During the course of the study, the animals were observed for overt toxicity and any existing test site abnormalities, including redness, bleeding, swelling, discharge, bruising and Test Article extrusion at the injection site were observed and recorded. In addition, injection weights were recorded at administration and body weights were taken and recorded at administration and at termination. At selected time points, five rats per Test Article were anesthetized and bled (about 5 mL) via cardiac puncture. Blood was collected in labeled potassium EDTA tubes. The blood was centrifuged for 10 min at 3000 rpm. The plasma fraction was transferred to a labeled 5 mL plastic culture tube and stored at −20 degrees C. Rat plasma samples were analyzed for buprenorphine concentration using a procedure described below.

After blood collection, the rat was sacrificed in a carbon dioxide chamber. The injection site was cut open and the drug residue and the surrounding tissues were carefully removed and placed in a scintillation vial. The vials were stored at −20 degrees C. until analysis. The retrieved drug residue/tissue was analyzed for buprenorphine content using the buprenorphine analysis method described below.

Buprenorphine Analysis in Rat Plasma Samples: This procedure was based on the method described by Li-Heng Pao et al., Journal of Chromatography B, 746:241-247 (2000). High Performance Liquid Chromatography had the following conditions: Mobile Phase: 80/20 acetonitrile/5 mM sodium acetate buffer (pH 3.75); flow rate: 1.2 mL/min;

autosampler temperature: room temperature; column temperature: 25° C.; detection: fluorescence (excitation at 215 nm and emission at 355 nm); total run time: 12 min; injection volume: 50 µL; column: Phenomenex Luna Silica (2) 250×4.6 mm, 5 µm; column storage: 100% acetonitrile; approximate retention time for buprenorphine and the internal standard: 7.3 min and 7.9 min.

Buprenorphine Extraction/Analysis Procedure: To the vials containing the retrieved drug residue/tissue, 10 mL of the formulation dissolution solution [90/5/5 acetonitrile/glacial acetic acid/water] was added. The vials were then shaken at 200 rpm at room temperature on an orbital shaker for at least 2 hours. The vials were then centrifuged at 2500 rpm for 10 minutes. After centrifuge, the vials were removed from the centrifuge. A portion of the supernatant from the vial was transferred into a HPLC vial and if necessary, the transferred solution in the vial was further diluted using the formulation dissolution solution to a suitable concentration for HPLC analysis.

The High Performance Liquid Chromatography had the following conditions: Mobile Phase A: 0.065% sodium octanesulfonic acid and 0.1% trifluoroacetic acid in water; Mobile Phase B: 90/10 acetonitrile/0.065% sodium octanesulfonic acid and 0.1% trifluoroacetic acid in water; flow rate: 1.0 ml/min; autosampler temperature: room temperature; column temperature: 30° C.; detection: 285 run (UV); total run time: 21 min; injection volume: 20 µL; column: Phenomenex Luna C18 250×4.6 mm, 5 µm; column storage: 70/30 acetonitrile/water; each sample run according to the following gradient program:

| Time (Minute) | Mobile Phase A | Mobile Phase B |
| --- | --- | --- |
| 0 | 100% | 0% |
| 2 | 100% | 0% |
| 16 | 20% | 80% |
| 18 | 0% | 100% |
| 20 | 100% | 0% |
| 21 | 100% | 0% |

As can be seen from the table above, buprenorphine had an approximate retention time of 16.8 minutes.

Preparation of standard solutions was conducted as follows: standard stock solution was made by dissolving approximately 10 mg buprenorphine in 10 mL 0.2% acetic acid aqueous solution. A series standards ranging from 40 ppm to 500 ppm were prepared by diluting proper amount of the standard stock solution in HPLC vials with water.

The dog study was conducted in male beagles with body weight in the range of 8-12 kg. Six dogs per group were injected subcutaneously in the dorsal thoracic region at a buprenorphine equivalent dose of 10 mg to 60 mg per dog, depending on the study design. Exact injection doses were obtained by weighing the injection syringe before and after each injection. After injection, the dogs were bled periodically via jugular vein into EDTA tubes. Plasma samples were then derived and stored in a −20° C. freezer until analysis. Dogs were weighed once daily on blood collection time points. The test sites were evaluated for any abnormalities including redness, bleeding, swelling, discharge, bruising, and TA extrusion on blood collection days. Dogs were also observed post-administration for signs of overt toxicity throughout the entire study period.

Buprenorphine Analysis in Dog Plasma Samples: Plasma samples from dog studies were analyzed for buprenorphine and norbuprenorphine levels using a liquid-liquid extraction step followed by LC-MS-MS analysis.

Example 1: Measurement of Buprenorphine Solubility in Biocompatible Solvents

Excess amount of buprenorphine or buprenorphine hydrochloride was weighed into a 1.8 cc HPLC vial containing about 0.5 g selected solvent. The vial was capped and placed on a jar mill rotating at 100 rpm at room temperature overnight. It was then centrifuged and part of top clear solution was weighed out and diluted in 1% acetic acid aqueous solution. Buprenorphine content in the solution was measured using the HPLC method described above.

TABLE 1

Buprenorphine Solubility in Various Solvents and Solvent Mixtures

| Solvent/Solvent Mixture | Buprenorphine Solubility (%, w/w) |
| --- | --- |
| NMP | 60.9 |
| DMSO | 55.0 |
| DMAC | 61.5 |
| 80/20 NMP/Propylene glycol (w/w) | 45.5 |
| 70/30 NMP/Propylene glycol (w/w) | 35.9 |
| 60/40 NMP/Propylene glycol (w/w) | 24.7 |
| 50/50 NMP/Propylene glycol (w/w) | 14.3 |
| 80/20 NMP/PEG400 (w/w) | 55.0 |
| 70/30 NMP/PEG400 (w/w) | 47.3 |
| 60/40 NMP/PEG400 (w/w) | 39.8 |
| 50/50 NMP/PEG400 (w/w) | 30.7 |
| 40/60 NMP/PEG400 (w/w) | 20.6 |
| 30/70 NMP/PEG400 (w/w) | 12.4 |
| 20/80 NMP/PEG400 (w/w) | 6.6 |
| 80/20 NMP/PEG300 (w/w) | 52.1 |
| 70/30 NMP/PEG300 (w/w) | 45.9 |
| 60/40 NMP/PEG300 (w/w) | 37.4 |
| 50/50 NMP/PEG300 (w/w) | 28.2 |
| 40/60 NMP/PEG300 (w/w) | 18.8 |
| 30/70 NMP/PEG300 (w/w) | 10.9 |
| 20/80 NMP/PEG300 (w/w) | 5.9 |
| 80/20 NMP/water (w/w) | 6.2 |

TABLE 2

Buprenorphine Hydrochloride Solubility in Various Solvents and Solvent Mixture

| Solvent/Solvent Mixture | Buprenorphine HCl Solubility (%, w/w) |
| --- | --- |
| NMP | 17.9 |
| DMSO | 19.7 |
| DMAC | 11.3 |
| 80/20 NMP/water (w/w) | 14.9 |

Tables 1 and 2 show that a solution containing more than 50% buprenorphine (w/w) can be prepared at room temperature using NMP, DMSO, or DMAC as the solvent. Even buprenorphine hydrochloride solution can be prepared at more than 10% by weight in NMP, DMSO, or DMAC.

Example 2: Preparation of 20 wt % and 40 wt % Buprenorphine Solutions in NMP 0.630 g and 0.840 g buprenorphine free base were weighed into two separate 1-drum vials. 2.520 g and 1.260 g NMP were then added to each vial accordingly. The vials were shaken and vortexed until complete dissolution of the drug. Each solution was then loaded into a 3 cc syringe and a sterile 0.2µ PTFE syringe tip filter was attached to the syringe. The solution was then filtered and the filtrate was filled into several 1 cc glass ampoules. The ampoules were then hermetically sealed with an open flame.

Example 3: Initial Burst Studies in Rats

In the first rat study, seven NMP solutions at buprenorphine concentrations ranging from 1% to 40% were injected subcutaneously in the DT region of the rats. At 24 hours, the rats were anesthetized and blood samples (about 5 mL) were taken via cardiac puncture. The rats were then sacrificed and the drug residues in each rat were removed. Both plasma and drug residue samples were analyzed for buprenorphine content. Results are shown in Tables 3 and 4.

TABLE 3

Percent of Buprenorphine Released at 24 Hours (Initial Burst) in Rats

| Buprenorphine Solution | Initial Burst (%) |
| --- | --- |
| 1% in NMP | 80.1 ± 6.0 |
| 3% in NMP | 38.7 ± 17.0 |
| 5% in NMP | 29.9 ± 18.0 |
| 10% in NMP | 22.1 ± 16.2 |
| 20% in NMP | 6.7 ± 2.8 |
| 30% in NMP | 4.8 ± 6.5 |
| 40% in NMP | 0.9 ± 2.0 |

TABLE 4

Buprenorphine Plasma Levels at 24 Hours

| Buprenorphine Solution | Plasma Level (ng/mL) |
| --- | --- |
| 1% in NMP | 6.1 ± 2.5 |
| 3% in NMP | 8.0 ± 2.6 |
| 5% in NMP | 10.6 ± 2.0 |
| 10% in NMP | 9.6 ± 2.1 |
| 20% in NMP | 15.8 ± 6.6 |
| 30% in NMP | 13.0 ± 3.3 |
| 40% in NMP | 12.4 ± 3.1 |

In the second rat study, six buprenorphine solutions in various solvents or solvent mixtures were investigated in a similar 24-hour rat study as the first rat study. Results are shown in Tables 5 and 6.

TABLE 5

Percent of Buprenorphine Released at 24 Hours (Initial Burst) in Rats

| Buprenorphine Solution | Initial Burst (%) |
| --- | --- |
| 50% in NMP | 4.4 ± 1.1 |
| 20% in DMSO | 9.7 ± 2.8 |
| 20% in DMAC | 8.2 ± 3.6 |
| 20% in 80/20 NMP/propylene glycol | 8.9 ± 2.5 |
| 20% in 80/20 NMP/PEG400 | 6.9 ± 1.3 |
| 20% in 91/9 NMP/water | 6.5 ± 2.9 |

TABLE 6

Buprenorphine Plasma Levels at 24 Hours

| Buprenorphine Solution | Plasma Level (ng/mL) |
| --- | --- |
| 50% in NMP | 21.9 ± 3.3 |
| 20% in DMSO | 20.0 ± 6.1 |
| 20% in DMAC | 23.6 ± 5.5 |
| 20% in 80/20 NMP/propylene glycol | 17.0 ± 0.6 |
| 20% in 80/20 NMP/PEG400 | 17.7 ± 3.9 |

TABLE 6-continued

Buprenorphine Plasma Levels at 24 Hours

| Buprenorphine Solution | Plasma Level (ng/mL) |
| --- | --- |
| 20% in 91/9 NMP/water | 17.2 ± 4.3 |
| 40% in NMP | 12.4 ± 3.1 |

The above results indicate that buprenorphine initial burst is highly dependent on buprenorphine content of the solution. Initial burst was large when buprenorphine concentration was below 5%. However, when buprenorphine concentration is 20% or higher, initial burst will be below 10% regardless of the solvent used in preparation of the buprenorphine solutions.

In a third burst study, four buprenorphine hydrochloride solutions were injected subcutaneously in rats. Initial burst results are shown in Table 7.

TABLE 7

Percent of Buprenorphine Hydrochloride Released at 24 Hours (Initial Burst) in Rats

| Buprenorphine HCl Solution | Initial Burst (%) |
| --- | --- |
| 10% in NMP | 28.7 ± 5.0 |
| 10% in DMSO | 34.3 ± 3.4 |
| 10% in DMAC | 35.0 ± 6.3 |
| 10% in 80/20 NMP/water | 36.5 ± 6.4 |

Although a large portion of buprenorphine hydrochloride still remains at the injection site after 24 hours, initial bursts are higher compared to buprenorphine solutions.

Example 4: 56-Day Buprenorphine Release Study in Rats

Two solution formulations with 20% buprenorphine by weight were injected subcutaneously in the rats. The first formulation is a NMP solution while the second formulation employed a solvent mixture of 1:1 NMP and propylene glycol (w/w). Both plasma samples and drug residue samples removed from the injection sites were analyzed. Release results from retrieved drug residues are shown in Table 8. Table 9 shows buprenorphine plasma levels over time. The data are also depicted in FIG. 1.

TABLE 8

Percent of Buprenorphine Released Based on Retrieved Drug Residue

| Time (Days) | 20% Buprenorphine in NMP | 20% Buprenorphine in 1:1 NMP/Propylene Glycol |
| --- | --- | --- |
| 1 | 10.2 ± 4.8 | 1.8 ± 1.9 |
| 7 | 7.7 ± 2.3 | 6.3 ± 6.1 |
| 14 | 15.7 ± 4.2 | 20.6 ± 3.9 |
| 21 | 26.5 ± 6.8 | 27.9 ± 9.9 |
| 28 | 33.0 ± 7.5 | 32.9 ± 16.8 |
| 42 | 62.7 ± 13.7 | 43.5 ± 6.5 |
| 56 | 68.4 ± 8.8 | 60.1 ± 6.2 |

TABLE 9

Buprenorphine Plasma Levels

| Time (Days) | 20% Buprenorphine in NMP (ng/mL) | 20% Buprenorphine in 1:1 NMP/Propylene Glycol (ng/mL) |
|---|---|---|
| 1 | 29.7 ± 10.0 | 26.9 ± 10.4 |
| 7 | 17.0 ± 4.0 | 13.5 ± 10.2 |
| 14 | 19.4 ± 6.3 | 37.2 ± 12.1 |
| 21 | 24.0 ± 14.1 | 23.5 ± 12.1 |
| 28 | 17.9 ± 8.9 | 18.1 ± 13.0 |
| 42 | 29.7 ± 3.6 | 20.8 ± 9.9 |
| 56 | 18.1 ± 4.1 | 24.9 ± 8.3 |

Buprenorphine plasma levels were maintained steady during the entire 56-day study period for both formulations. In addition, there were still substantial amount of buprenorphine remaining at the injection site after 56 days.

Example 5: First Pharmacokinetics Study in Beagle Dogs

Figure 2:
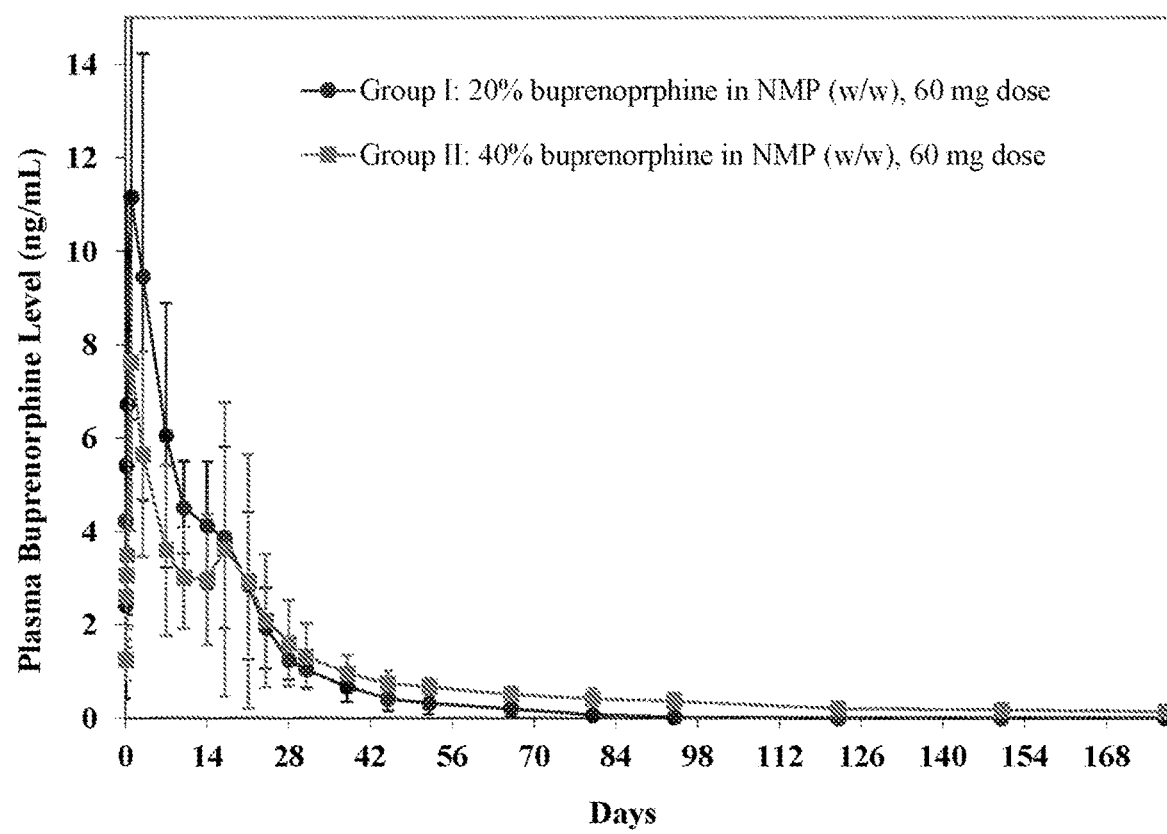
FIG. 2 illustrates buprenorphine plasma profiles after subcutaneous injection of two buprenorphine solutions at 60 mg buprenorphine dose in two groups of dogs.

Two solutions with 20% and 40% buprenorphine in NMP by weight were injected subcutaneously in the dorsal thoracic region at a dose of 60 mg buprenorphine per dog. Blood samples were collected periodically from jugular vein and plasma samples were derived and kept in frozen until analysis. Plasma samples were analyzed for both buprenorphine and norbuprenorphine levels using a validated LC-MS-MS method. Assay results are listed in Table 10 and also depicted in FIG. 2. Results show that both formulations were able to maintain buprenorphine plasma levels above 1.0 ng/mL for 31 days.

Table 10. Buprenorphine and Norbuprenorphine Plasma Levels (Mean±SD) after SC Injection of Buprenorphine NMP Solutions

| Group I: 20% buprenorphine in NMP | | | | |
|---|---|---|---|---|
| Time (Day) | Buprenorphine (ng/mL) | SD | Norbuprenorphine (ng/mL) | SD |
| −1 | BLQ < (0.100) | N/A | BLQ < (0.0800) | N/A |
| 1 hr | 2.42 | 2.01 | 0.533 | 0.151 |
| 2 hr | 4.23 | 2.70 | 0.511 | 0.164 |
| 4 hr | 5.42 | 3.43 | 0.354 | 0.133 |
| 8 hr | 6.72 | 4.51 | 0.140 | 0.084 |
| 1 | 11.2 | 4.76 | 0.0722 | 0.0794 |
| 3 | 9.45 | 4.78 | 0.0870 | 0.1017 |
| 7 | 6.06 | 2.83 | 0.0323 | 0.0501 |
| 10 | 4.52 | 0.99 | 0.0142 | 0.0348 |
| 14 | 4.13 | 1.37 | BLQ < (0.0800) | N/A |
| 17 | 3.87 | 1.94 | BLQ < (0.0800) | N/A |
| 21 | 2.84 | 1.58 | BLQ < (0.0800) | N/A |
| 24 | 1.93 | 0.87 | BLQ < (0.0800) | N/A |
| 28 | 1.24 | 0.41 | BLQ < (0.0800) | N/A |
| 31 | 1.04 | 0.40 | BLQ < (0.0800) | N/A |
| 38 | 0.668 | 0.324 | BLQ < (0.0800) | N/A |
| 45 | 0.418 | 0.260 | BLQ < (0.0800) | N/A |
| 52 | 0.318 | 0.242 | BLQ < (0.0800) | N/A |
| 66 | 0.198 | 0.177 | BLQ < (0.0800) | N/A |
| 80 | 0.0693 | 0.0847 | BLQ < (0.0800) | N/A |
| 94 | 0.0208 | 0.0510 | BLQ < (0.0800) | N/A |
| 122 | BLQ < (0.100) | N/A | BLQ < (0.0800) | N/A |
| 150 | 0.0202 | 0.0494 | BLQ < (0.0800) | N/A |
| 178 | BLQ < (0.100) | N/A | BLQ < (0.0800) | N/A |

| Group II: 40% buprenorphine in NMP | | | | |
|---|---|---|---|---|
| Time (Day) | Buprenorphine (ng/mL) | SD | Norbuprenorphine (ng/mL) | SD |
| −1 | BLQ < (0.100) | N/A | BLQ < (0.0800) | N/A |
| 1 hr | 1.25 | 0.46 | 0.253 | 0.149 |
| 2 hr | 2.60 | 0.95 | 0.227 | 0.139 |
| 4 hr | 3.06 | 1.16 | 0.136 | 0.094 |
| 8 hr | 3.50 | 1.53 | 0.0326 | 0.0506 |
| 1 | 7.63 | 3.61 | 0.0167 | 0.0408 |
| 3 | 5.65 | 2.20 | 0.0530 | 0.0849 |
| 7 | 3.60 | 1.83 | BLQ < (0.0800) | N/A |
| 10 | 3.01 | 1.09 | 0.0182 | 0.0445 |
| 14 | 2.96 | 1.39 | BLQ < (0.0800) | N/A |
| 17 | 3.62 | 3.15 | BLQ < (0.0800) | N/A |
| 21 | 2.93 | 2.72 | BLQ < (0.0800) | N/A |
| 24 | 2.08 | 1.42 | BLQ < (0.0800) | N/A |
| 28 | 1.61 | 0.92 | BLQ < (0.0800) | N/A |
| 31 | 1.32 | 0.70 | BLQ < (0.0800) | N/A |
| 38 | 0.958 | 0.382 | BLQ < (0.0800) | N/A |
| 45 | 0.749 | 0.267 | BLQ < (0.0800) | N/A |
| 52 | 0.668 | 0.180 | BLQ < (0.0800) | N/A |
| 66 | 0.508 | 0.171 | BLQ < (0.0800) | N/A |
| 80 | 0.412 | 0.225 | BLQ < (0.0800) | N/A |
| 94 | 0.359 | 0.175 | BLQ < (0.0800) | N/A |

-continued

| Group II: 40% buprenorphine in NMP | | | | |
|---|---|---|---|---|
| Time (Day) | Buprenorphine (ng/mL) | SD | Norbuprenorphine (ng/mL) | SD |
| 122 | 0.207 | 0.122 | BLQ < (0.0800) | N/A |
| 150 | 0.176 | 0.100 | BLQ < (0.0800) | N/A |
| 178 | 0.136 | 0.076 | BLQ < (0.0800) | N/A |

The above example shows that both NMP solutions had very low initial bursts of below 5% estimated from the ratio of area under the curve (AUC) in the initial 24 hours over total AUC up to 178 days. The formulations yielded comparable total AUCs and there were no visible local tissue reactions or systematic toxicities except the known side effects of buprenorphine.

Example 6: Second Pharmacokinetics Study in Beagle Dogs

Figure 3:
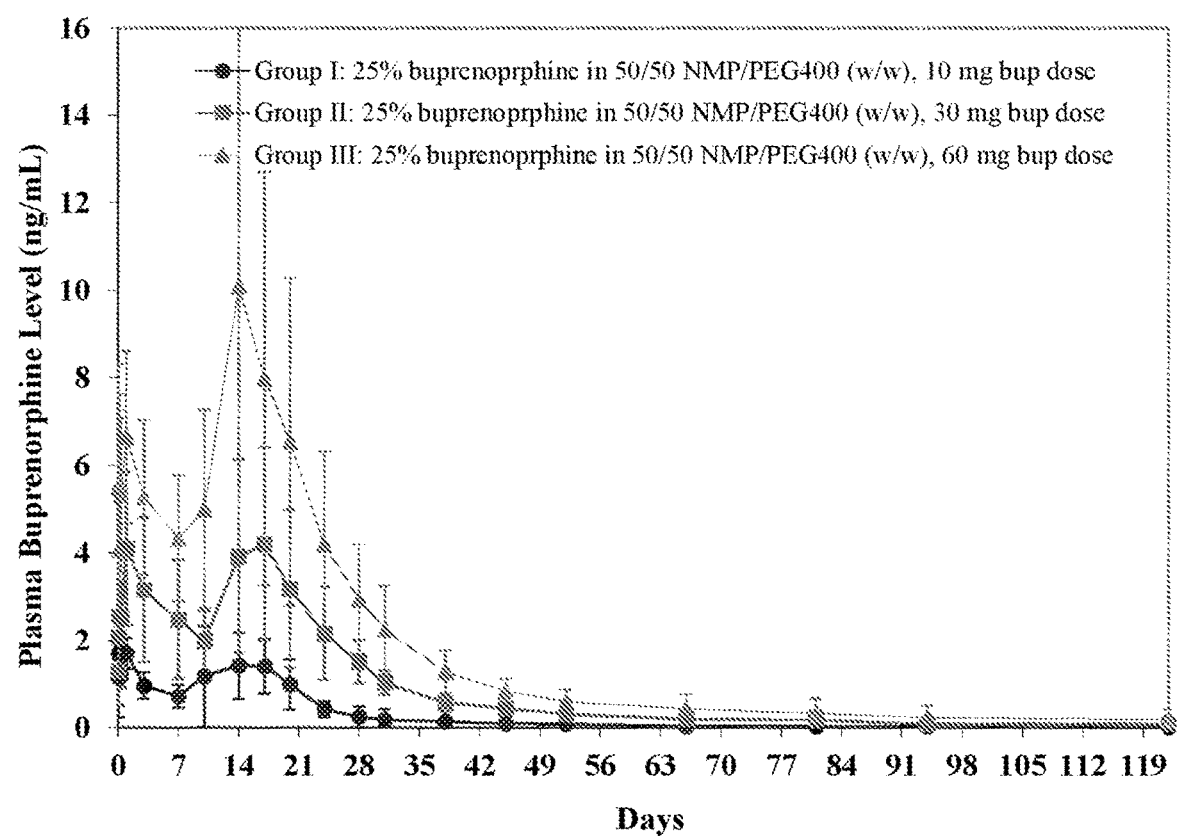
FIG. 3 illustrates buprenorphine plasma profiles after subcutaneous injection of a 25 wt % buprenorphine solution at buprenorphine doses of 10 mg, 30 mg, and 60 mg in three groups of dogs.

A solution with 25 wt % buprenorphine in a 50/50 NMP/PEG400 solvent mixture by weight was prepared by simply dissolving buprenorphine in the solvent mixture. The solution was then sterile filtered into empty sealed sterile and pyrogen free vials. The solution was injected subcutaneously in the dorsal thoracic region to three groups of beagles at 10 mg, 30 mg, and 60 mg buprenorphine per dog. Blood samples were collected periodically from jugular vein and plasma samples were derived and kept in frozen until analysis. Plasma samples were analyzed for both buprenorphine and norbuprenorphine levels using a validated LC-MS-MS method. Buprenorphine plasma levels are listed in Table 11 and the data are also depicted in FIG. 3. Norbuprenorphine levels were not listed because the levels were very low and inconsequential. Results show that steady plasma buprenorphine levels were maintained for 28 days at their respective levels for all three groups.

TABLE 11

Buprenorphine Plasma Levels (Mean ± SD) after SC Injection of the Same Buprenorphine Solution at Three Different Doses in Dogs

| Time (Day) | Group I (10 mg) | SD | Group II (30 mg) | SD | Group III (60 mg) | SD |
|---|---|---|---|---|---|---|
| −1 | BLQ < (0.100) | N/A | BLQ < (0.100) | N/A | BLQ < (0.100) | N/A |
| 1 hr | 1.13 | 0.89 | 1.30 | 0.80 | 4.08 | 3.18 |
| 2 hr | 1.68 | 1.17 | 2.07 | 1.14 | 5.48 | 2.83 |
| 4 hr | 1.73 | 0.80 | 2.55 | 1.14 | 5.58 | 2.03 |
| 8 hr | 1.18 | 0.27 | 2.50 | 0.89 | 5.32 | 1.76 |
| 1 | 1.70 | 0.36 | 4.10 | 1.75 | 6.65 | 1.97 |
| 3 | 0.958 | 0.298 | 3.15 | 1.66 | 5.27 | 1.77 |
| 7 | 0.715 | 0.262 | 2.48 | 1.37 | 4.33 | 1.44 |
| 10 | 1.17 | 1.17 | 1.99 | 0.70 | 5.00 | 2.27 |
| 14 | 1.41 | 0.77 | 3.92 | 2.21 | 10.1 | 6.1 |
| 17 | 1.40 | 0.62 | 4.21 | 2.20 | 7.98 | 4.72 |
| 20 | 0.983 | 0.570 | 3.17 | 1.81 | 6.54 | 3.74 |
| 24 | 0.418 | 0.179 | 2.16 | 1.07 | 4.19 | 2.13 |
| 28 | 0.243 | 0.239 | 1.50 | 0.50 | 2.94 | 1.25 |
| 31 | 0.183 | 0.241 | 1.03 | 0.27 | 2.24 | 1.01 |
| 38 | 0.134 | 0.276 | 0.566 | 0.199 | 1.27 | 0.49 |
| 45 | 0.0898 | 0.2200 | 0.436 | 0.309 | 0.839 | 0.265 |
| 52 | 0.0738 | 0.1809 | 0.309 | 0.296 | 0.586 | 0.281 |
| 66 | 0.0347 | 0.0849 | 0.194 | 0.180 | 0.431 | 0.333 |
| 81 | 0.0278 | 0.0682 | 0.174 | 0.187 | 0.319 | 0.339 |
| 94 | 0.0217 | 0.0531 | 0.0802 | 0.1292 | 0.229 | 0.273 |
| 122 | BLQ < (0.100) | N/A | 0.0758 | 0.1858 | 0.184 | 0.231 |

Key pharmacokinetic parameters were derived for all three groups and the parameters are listed in Table 12. Notably, all three groups had a very low initial burst that was less than 5%. Moreover, both of their initial and plateau plasma levels (Initial $C_{max}$ and Plateau $C_{max}$) were only about twice as high as their respective average levels in 28 days ($C_{Ave0-28d}$) indicating very steady plasma levels over the 28 day period. Most importantly, both $C_{Ave0-28d}$ and $AUC_{0-122d}$ values for the three groups showed a ratio very close to the dose ratio of 1:3:6 demonstrating that the increase in plasma levels was proportional to increase in doses for this buprenorphine solution formulation.

TABLE 12

Mean (± Standard Deviation) Buprenorphine Pharmacokinetic Parameters for Each Group

| Parameters | Unit | Group I (10 mg) | Group II (30 mg) | Group III (60 mg) |
|---|---|---|---|---|
| Initial $t_{max}$ | Hours | 14 | 24 | 14 |
| Initial $C_{max}$ | ng/mL | 2.21 ± 0.86 | 4.33 ± 1.57 | 7.18 ± 2.43 |
| Plateau $t_{max}$ | Days | 17 | 15.5 | 14 |
| Plateau $C_{max}$ | Ng/mL | 2.04 ± 0.92 | 5.37 ± 1.92 | 10.5 ± 5.7 |
| $AUC_{0-1d}$ | ng/mL * Day | 1.43 ± 0.29 | 2.91 ± 1.06 | 5.64 ± 1.72 |
| $AUC_{0-122d}$ | ng/mL * Day | 32.3 ± 7.3 | 81.2 ± 25.5 | 166 ± 69 |
| Initial Burst | % | 4.7± 1.6 | 2.7 ± 0.7 | 2.6 ± 0.5 |
| $C_{Ave0-28d}$ | ng/mL | 0.976 ± 0.262 | 2.90 ± 0.91 | 5.91 ± 2.45 |
| $t_{min1-28d}$ | Days | 28 | 26 | 28 |
| $C_{min1-28d}$ | ng/mL | 0.195 ± 0.139 | 1.20 ± 0.29 | 2.94 ± 1.25 |

With reference to Table 12, initial maximum plasma level (Initial $C_{max}$) is the peak plasma concentration reached for each animal within the first 24 hours. Initial $C_{max}$ for each group is the average Initial $C_{max}$ of that group. Initial $t_{max}$ is the time to reach the initial peak plasma concentration for each animal and Initial $t_{max}$ for each group is the median $t_{max}$ for that group. Plateau maximum level (Plateau $C_{max}$) is the secondary plasma peak reached after Day 1 and Plateau $t_{max}$ is the time to reach the secondary peak plasma levels. Area under the curve (AUC) was calculated using the trapezoidal method. Initial burst in the first 24 hours is the ratio of $AUC_{0-1d}$ over $AUC_{0-122d}$. Average plasma level in the first 28 days ($C_{Ave0-28d}$) was calculated using $AUC_{0-28d}$ divided by 28 days. $C_{min1d-28d}$ is the lowest plasma level from Day 1 to Day 28 after injection. $C_{min1d-28d}$ for each group is the average $C_{min1d-28d}$ of that group. The $t_{min1d-28d}$ is the time to reach the lowest plasma level during the Day 1 to Day 28 period and $t_{min1d-28d}$ for each group is the median $t_{min1d-28d}$ of that group.

Example 7: Third Pharmacokinetics Study in Beagle Dogs

Figure 4:
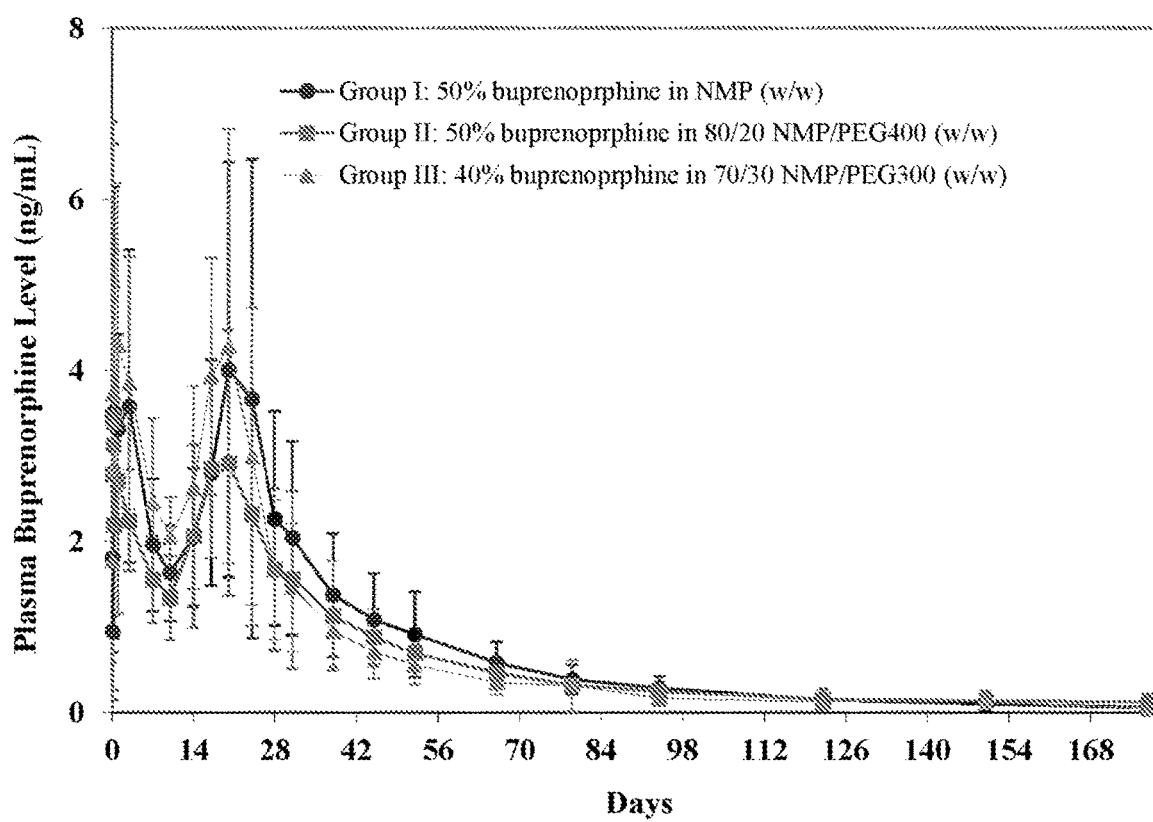
FIG. 4 illustrates buprenorphine plasma profiles after subcutaneous injection of three different buprenorphine solutions at a buprenorphine dose of 60 mg in three groups of dogs.

Three buprenorphine solution formulations were prepared in sterile and pyrogen free vials after sterile filtration. The three formulations had the following composition: (1) 50 wt % buprenorphine in NMP; (2) 50 wt % buprenorphine in 80/20 NMP/PEG400 (w/w); and (3) 40 wt % buprenorphine in 70/30 NMP/PEG300 (w/w). All three solutions were injected subcutaneously in the dorsal thoracic region to three separate groups of beagles at the same dose of 60 mg buprenorphine per dog. Blood samples were collected periodically from jugular vein and plasma samples were derived and kept in frozen until analysis. Plasma samples were analyzed for both buprenorphine and norbuprenorphine levels using a validated LC-MS-MS method. Buprenorphine plasma levels are listed in Table 13 and the data are also depicted in FIG. 4. Norbuprenorphine levels were not listed because the levels were very low and inconsequential. Results show that all three formulations yielded similar plasma profiles. Their PK parameters (see Table 14) also show these formulations had very similar performances in dogs. All three solution formulations yielded very steady plasma levels with their ratios of $C_{max}$ over $C_{min\ 1-28d}$ smaller than 4 and their $C_{min\ 1-28d}$ above 1.0 ng/mL. These formulations also produced very low initial bursts of less than 3%.

TABLE 13

Buprenorphine Plasma Levels (Mean ± SD) after SC Injection of Three Buprenorphine Solutions at the Same Dose of 60 mg Buprenorphine in Dogs

| Time (Day) | Group I (50% in NMP) | SD | Group II (50% in 80/20 NMP/PEG400) | SD | Group III (40% in 70/30 NMP/PEG300) | SD |
|---|---|---|---|---|---|---|
| −1 | BLQ < (0.100) | N/A | BLQ < (0.100) | N/A | BLQ < (0.100) | N/A |
| 1 hr | 0.945 | 0.797 | 2.78 | 4.12 | 1.78 | 1.19 |
| 2 hr | 1.80 | 1.10 | 3.45 | 3.19 | 2.85 | 1.07 |
| 4 hr | 3.12 | 2.26 | 3.12 | 1.92 | 3.73 | 1.09 |
| 8 hr | 3.52 | 2.63 | 2.19 | 1.06 | 3.40 | 1.57 |
| 1 | 3.31 | 1.10 | 2.72 | 1.56 | 4.30 | 1.89 |
| 3 | 3.58 | 1.83 | 2.25 | 0.59 | 3.85 | 1.47 |
| 7 | 1.96 | 0.78 | 1.55 | 0.51 | 2.47 | 0.97 |
| 10 | 1.63 | 0.56 | 1.34 | 0.49 | 2.05 | 0.47 |
| 14 | 2.05 | 0.81 | 2.06 | 1.07 | 2.63 | 1.19 |
| 17 | 2.80 | 1.32 | 2.86 | 1.05 | 3.93 | 1.38 |
| 20 | 4.01 | 2.43 | 2.92 | 1.55 | 4.28 | 2.54 |
| 24 | 3.67 | 2.80 | 2.32 | 1.31 | 2.99 | 1.74 |
| 28 | 2.27 | 1.25 | 1.67 | 0.95 | 1.67 | 0.82 |
| 31 | 2.04 | 1.14 | 1.55 | 1.04 | 1.47 | 0.75 |
| 38 | 1.37 | 0.72 | 1.13 | 0.64 | 0.948 | 0.420 |
| 45 | 1.08 | 0.54 | 0.879 | 0.324 | 0.708 | 0.312 |
| 52 | 0.911 | 0.498 | 0.689 | 0.164 | 0.561 | 0.238 |
| 66 | 0.581 | 0.242 | 0.463 | 0.105 | 0.348 | 0.140 |
| 79 | 0.387 | 0.173 | 0.321 | 0.065 | 0.313 | 0.300 |
| 94 | 0.2848 | 0.1372 | 0.2457 | 0.0680 | 0.1650 | 0.0869 |
| 122 | 0.1478 | 0.1283 | 0.1565 | 0.1239 | 0.1253 | 0.0645 |
| 150 | 0.0978 | 0.1146 | 0.1367 | 0.1114 | 0.1230 | 0.0693 |
| 178 | 0.0568 | 0.0880 | 0.1198 | 0.0947 | 0.0453 | 0.0710 |

TABLE 14

Mean (± Standard Deviation) Buprenorphine Pharmacokinetic Parameters

| Parameters | Unit | Group I (50% in NMP) | Group II (50% in 80/20 NMP/PEG400) | Group III (40% in 70/30 NMP/PEG300) |
|---|---|---|---|---|
| Initial $t_{max}$ | Hours | 1 | 0.58 | 1 |
| Initial $C_{max}$ | ng/mL | 4.22 ± 2.28 | 4.78 ± 3.43 | 4.62 ± 1.60 |
| Plateau $t_{max}$ | Days | 20 | 18.5 | 18.5 |
| Plateau $C_{max}$ | Ng/mL | 5.16 ± 2.51 | 3.61 ± 1.09 | 5.47 ± 1.39 |
| $AUC_{0-1d}$ | ng/mL * Day | 3.11 ± 1.73 | 2.54 ± 1.26 | 3.56 ± 1.36 |
| $AUC_{0-178d}$ | ng/mL * Day | 146 ± 49 | 118 ± 24 | 134 ± 34 |
| Initial Burst | % | 2.1 ± 1.0 | 2.1 ± 0.9 | 2.7 ± 0.9 |
| $C_{Ave0-28d}$ | ng/mL | 2.80 ± 1.23 | 2.17 ± 0.81 | 3.09 ± 0.83 |
| $t_{min1-28d}$ | Days | 10 | 21 | 28 |
| $C_{min1-28d}$ | ng/mL | 1.36 ± 0.61 | 1.21 ± 0.48 | 1.41 ± 0.52 |

With reference to Table 14, initial maximum plasma level (Initial $C_{max}$) is the peak plasma concentration reached for each animal within the first 24 hours. Initial $C_{max}$ for each group is the average Initial $C_{max}$ of that group. Initial $t_{max}$ is the time to reach the initial peak plasma concentration for each animal and Initial $t_{max}$ for each group is the median $t_{max}$ for that group. Plateau maximum level (Plateau $C_{max}$) is the secondary plasma peak reached after Day 1 and Plateau $t_{max}$ is the time to reach the secondary peak plasma levels. Area under the curve (AUC) was calculated using the trapezoidal method. Initial burst in the first 24 hours is the ratio of $AUC_{0-1d}$ over $AUC_{0-178d}$. Average plasma level in the first 28 days ($C_{Ave0-28d}$) was calculated using $AUC_{0-28d}$ divided by 28 days. $C_{min1-28d}$ is the lowest plasma level from Day 1 to Day 28 after injection. $C_{min1-28d}$ for each group is the average $C_{min1-28d}$ of that group. The $t_{min1-28d}$ is the time to reach the lowest plasma level during the Day 1 to Day 28 period and $t_{min1-28d}$ for each group is the median $t_{min1-28d}$ of that group.

The present invention also realizes the benefit of a small injection volume by utilizing the exceptionally high buprenorphine solubility of more than 50% in NMP, DMAC, or DMSO.

Without being bound by any theory, it is believed that the buprenorphine achieves a sustained release profile in the absence of release-modifying agents as a result of its low solubility in the aqueous environment in the subcutaneous space and the manner in which it precipitates out of the organic solvent or solvent mixture to form a distinct depot in the subcutaneous space in a living body.

The invention is further illustrated by the following numbered clauses.

Clause 1. A composition comprising a solution of 5-55 wt % of buprenorphine dissolved in a polar aprotic solvent selected from N-methyl-2-pyrrolidone (NMP), dimethyl acetamide (DMAC), or dimethyl sulfoxide (DMSO) wherein the composition does not comprise any biocompatible or biodegradable polymer.

Clause 2. A composition of clause 1 wherein the composition comprises from 10-50 wt % buprenorphine.

Clause 3. A composition of clause 2 wherein the composition comprises 20-40 wt % buprenorphine.

Clause 4. A composition of clause 3 wherein the composition comprises 30-40 wt % buprenorphine.

Clause 5. A composition of clause 1 wherein the buprenorphine is present as the free base (unprotonated) form or as a pharmaceutically acceptable salt.

Clause 6. A composition of clause 1 wherein the composition comprises up to 500 mg of buprenorphine.

Clause 7. A composition of clause 6 wherein the composition comprises up to 500 mg of buprenorphine in a 1 cc solution.

Clause 8. A composition of clause 6 wherein the composition comprises from 150-300 mg of buprenorphine.

Clause 9. A composition of clause 8 wherein the composition comprises from 150-300 mg of buprenorphine in 1 cc or less solution.

Clause 10. A composition of clause 6 wherein the composition comprises from 10-50 mg of buprenorphine.

Clause 11. A composition of clause 10 wherein the composition comprises from 10-50 mg of buprenorphine in 0.2 cc or less solution.

Clause 12. A composition of clause 1 wherein the composition further comprises up to 10% by weight of water.

Clause 13. A composition of clause 1 wherein the composition further comprises a glycol up to 70% by weight.

Clause 14. A composition of clause 13 wherein the amount of glycol is from 20-60% of the solvent mixture by weight.

Clause 15. A composition of clause 14 wherein the amount of glycol is from 20-40% of the solvent mixture by weight.

Clause 16. A composition of clause 15 wherein the amount of glycol is from 30-40% of the solvent mixture by weight.

Clause 17. A composition of clause 13 wherein the glycol is selected from PEG300, PEG400 or propylene glycol.

Clause 18. A composition of clause 13 wherein the ratio of polar aprotic solvent to glycol can be from 0.4:1 to 4:1.

Clause 19. A composition of clause 18 wherein the ratio is from 0.65:1 to 2.5:1.

Clause 20. A composition of clause 19 wherein the ratio is from 1:1 to 1.5:1.

Clause 21. A composition of clause 13 wherein the ratio of buprenorphine to glycol is from 0.15:1 to 5:1.

Clause 22. A composition of clause 21 wherein the ratio is from 0.4:1 to 3.5:1.

Clause 23. A composition of clause 21 wherein the ratio is from 0.5:1 to 1:1.

Clause 24. A composition of clause 13 wherein the composition comprises buprenorphine, a solvent selected from N-methyl-2-pyrrolidone (NMP), dimethyl acetamide (DMAC), or dimethyl sulfoxide (DMSO) and a glycol selected from PEG300, PEG400 or propylene glycol in a ratio of from 1:3:7 to 1:0.5:0.1.

Clause 25. A composition of clause 24 wherein the ratio is from 1:2:2 to 1:1:0.4.

Clause 26. A composition of clause 24 wherein the ratio is selected from 1:2.7:6.3, 1:1.5:1.5, 1:1.4:0.93, 1:1.05:0.45 or 1:0.8:0.2.

Clause 27. A composition of clause 24 wherein the composition consists essentially of buprenorphine, N-methyl-2-pyrrolidone (NMP) and PEG 400 in a ratio of from 1:3:7 to 1:0.5:0.1.

Clause 28. A composition of clause 27 wherein the ratio is from 1:2:2 to 1:1:0.4.

Clause 29. A composition of clause 27 wherein the ratio is selected from 1:2.7:6.3, 1:1.5:1.5, 1:1.4:0.93, 1:1.05:0.45 or 1:0.8:0.2.

Clause 30. A composition of clause 1 wherein the composition further comprises one or more pharmaceutically acceptable stabilizing antioxidant agents such as ascorbic acid, vitamin E, BHT, BHA which can enhance buprenorphine stability.

Clause 31. A method of treating a patient for opioid dependence or pain relief comprising administering subcutaneously a composition of clause 1.

Clause 32. A method of clause 31 wherein the method provides treatment for opioid dependence or pain relief over a period of at least 30 days.

Clause 33. A method of clause 31 wherein the method provides treatment for opioid dependence or pain relief over a period up to 3 months.

Clause 34. A method of clause 31 wherein the method provides a therapeutically effective dosage of the buprenorphine from about 0.10 mg to about 10 milligrams (mg) per day.

Clause 35. A method of clause 31 wherein the method provides a therapeutically effective level of the buprenorphine within about one day after administration of the composition; and wherein the therapeutically effective dosage of the buprenorphine, or a pharmaceutical acceptable salt thereof is delivered for at least one month after administration of the composition, or up to 3 months after administration of the composition.

Further modifications and improvements can be made without departing from the scope of the invention described herein.

What is claimed is:

1. An injectable pharmaceutical solution comprising about 10 wt % to about 45 wt % of buprenorphine free base and a solvent mixture; wherein the solvent mixture comprises N-methyl-2-pyrrolidone and about 10 wt % to about 70 wt % polyethylene glycol.

2. The solution of claim 1, comprising about 15 wt % to about 35 wt % of buprenorphine free base.

3. The solution of claim 2, comprising about 20 wt % of buprenorphine free base.

4. The solution of claim 2, comprising about 30 wt % of buprenorphine free base.

5. The solution of claim 1, wherein the solvent mixture comprises about 50 wt % to about 85 wt % of N-methyl-2-pyrrolidone and about 15 wt % to about 50 wt % of polyethylene glycol.

6. The solution of claim 5, wherein the solvent mixture comprises about 50 wt % to about 80 wt % of N-methyl-2-pyrrolidone and about 20 wt % to about 50 wt % of polyethylene glycol.

7. The solution of claim 6, wherein the solvent mixture comprises about 50 wt % to about 70 wt % of N-methyl-2-pyrrolidone and about 30 wt % to about 50 wt % of polyethylene glycol.

8. The solution of claim 6, wherein the solvent mixture comprises about 60 wt % to about 80 wt % of N-methyl-2-pyrrolidone and about 20 wt % to about 40 wt % of polyethylene glycol.

9. The solution of claim 8, wherein the solvent mixture comprises about 70 wt % to about 80 wt % of N-methyl-2-pyrrolidone and about 20 wt % to about 30 wt % of polyethylene glycol.

10. The solution of claim 1, wherein the polyethylene glycol has an average molecular weight from about 100 to about 1,000.

11. The solution of claim 10, wherein the polyethylene glycol has an average molecular weight of about 300.

12. The solution of claim 1, comprising about 20 wt % of buprenorphine free base; wherein the weight ratio of N-methyl-2-pyrrolidone to polyethylene glycol is about 60:40.

13. A method of treating opioid dependence in a patient in need thereof, the method comprising subcutaneously injecting the patient with a therapeutically effective amount of the solution of claim 1 to treat the opioid dependence.

14. The method of claim 13, comprising subcutaneously injecting the patient about once per month to about once every three months with the therapeutically effective amount of the solution.

15. An injectable pharmaceutical solution comprising about 20 wt % of buprenorphine free base and a solvent mixture; wherein the solvent mixture comprises N-methyl- 2-pyrrolidone and polyethylene glycol in a weight ratio of about 60:40; and wherein the polyethylene glycol has an average molecular weight of about 300.

16. A method of treating opioid dependence in a patient in need thereof, the method comprising subcutaneously injecting the patient with a therapeutically effective amount of the solution of claim 15 to treat the opioid dependence.

17. An injectable pharmaceutical solution comprising about 30 wt % of buprenorphine free base and a solvent mixture; wherein the solvent mixture comprises about 70 wt % to about 80 wt % of N-methyl-2-pyrrolidone and about 20 wt % to about 30 wt % of polyethylene glycol; and wherein the polyethylene glycol has an average molecular weight of about 300.

18. The solution of claim 17, wherein the solvent mixture comprises about 75 wt % of N-methyl-2-pyrrolidone and about 25 wt % of polyethylene glycol.

19. A method of treating opioid dependence in a patient in need thereof, the method comprising subcutaneously injecting the patient with a therapeutically effective amount of the solution of claim 17 to treat the opioid dependence.

20. An injectable pharmaceutical solution comprising about 20 wt % of buprenorphine free base and a solvent mixture; wherein the solvent mixture comprises about 70 wt % to about 80 wt % of N-methyl-2-pyrrolidone and about 20 wt % to about 30 wt % of polyethylene glycol; and wherein the polyethylene glycol has an average molecular weight of about 300.

21. The solution of claim 20, wherein the solvent mixture comprises about 75 wt % of N-methyl-2-pyrrolidone and about 25 wt % of polyethylene glycol.

22. A method of treating opioid dependence in a patient in need thereof, the method comprising subcutaneously injecting the patient with a therapeutically effective amount of the solution of claim 20 to treat the opioid dependence.

* * * * *